United States Patent
Thilagarajah

(10) Patent No.: US 10,721,534 B2
(45) Date of Patent: Jul. 21, 2020

(54) ONLINE COLLABORATION SYSTEMS AND METHODS

(71) Applicant: Context Systems LLP, Coggeshall, Essex (GB)

(72) Inventor: Ranjan Thilagarajah, Brighton (AU)

(73) Assignee: Context Systems LLP (GB)

( * ) Notice: Subject to any disclaimer, the term of this patent is extended or adjusted under 35 U.S.C. 154(b) by 0 days.

(21) Appl. No.: 15/543,441

(22) PCT Filed: Mar. 31, 2015

(86) PCT No.: PCT/AU2015/050139
§ 371 (c)(1),
(2) Date: Jul. 13, 2017

(87) PCT Pub. No.: WO2016/119005
PCT Pub. Date: Aug. 4, 2016

(65) Prior Publication Data
US 2017/0374425 A1    Dec. 28, 2017

(30) Foreign Application Priority Data
Jan. 28, 2015 (AU) ................................ 2015200410

(51) Int. Cl.
| H04N 21/4788 | (2011.01) |
| G16H 80/00 | (2018.01) |
| H04N 21/25 | (2011.01) |
| G06Q 10/10 | (2012.01) |
(Continued)

(52) U.S. Cl.
CPC ....... *H04N 21/4788* (2013.01); *G06F 3/0482* (2013.01); *G06F 3/0484* (2013.01);
(Continued)

(58) Field of Classification Search
CPC ............. H04N 21/4788; H04N 21/258; H04N 21/252; H04N 21/48; G06F 3/04842;
(Continued)

(56) References Cited

U.S. PATENT DOCUMENTS

| 7,362,349 B2 | 4/2008 | Nelson et al. |
| 2004/0006553 A1* | 1/2004 | de Vries ................. G16H 80/00 |
(Continued)

OTHER PUBLICATIONS

Null, C., "Adobe Connect upgraded to offer conference recording and mobile streaming," published Aug. 19, 2013 from: <URL:http://www.pcworld.com/article/2046838/adobe-connect-upgraded-to-offer-conference-recording-and-mobile-streaming.html> [retrieved from internet on Apr. 20, 2015.].

(Continued)

*Primary Examiner* — Yassin Alata
(74) *Attorney, Agent, or Firm* — Lerner, David, Littenberg, Krumholz & Mentlik, LLP

(57) ABSTRACT

An online collaboration system comprises at least one server in communication with multiple client computing devices over a communication network, the at least one server executing program code to host an online collaborative environment in which users of the client computing devices can collaborate. The at least one server executes program code to facilitate an online meeting between the users of the client computing devices in the online collaboration environment, display a plurality of conference panels on a user interface of at least some of the multiple client computing devices, each conference panel configured to depict a real-time video stream associated with one of the client computing devices participating in the online meeting and display at least one display panel on a user interface of at least some of the multiple client computing devices, wherein the at least one display panel of each user interface is configured to display common shared information relating to the online meeting.

21 Claims, 18 Drawing Sheets

(51) Int. Cl.
  *H04N 21/258* (2011.01)
  *G06Q 50/22* (2018.01)
  *G06F 3/0482* (2013.01)
  *G06F 3/0484* (2013.01)
  *G06F 3/147* (2006.01)
  *H04N 21/482* (2011.01)
  *G06F 3/0481* (2013.01)
  *G06F 3/16* (2006.01)

(52) U.S. Cl.
  CPC .......... *G06F 3/04842* (2013.01); *G06F 3/147* (2013.01); *G06Q 10/101* (2013.01); *G06Q 10/103* (2013.01); *G06Q 10/1095* (2013.01); *G06Q 50/22* (2013.01); *G16H 80/00* (2018.01); *H04N 21/252* (2013.01); *H04N 21/258* (2013.01); *H04N 21/482* (2013.01); *G06F 3/04817* (2013.01); *G06F 3/165* (2013.01); *G06F 2203/04803* (2013.01)

(58) Field of Classification Search
  CPC ...... G06F 3/147; G06F 3/0482; G06F 3/0484; G06F 3/165; G06F 3/04817
  See application file for complete search history.

(56) References Cited

U.S. PATENT DOCUMENTS

2006/0236247 A1* 10/2006 Morita ............... G06F 19/321
  715/733
2007/0285501 A1* 12/2007 Yim ..................... H04L 12/66
  348/14.08
2016/0165044 A1* 6/2016 Chan ................. H04M 3/42221
  455/413

OTHER PUBLICATIONS

International Search Report and Written Opinion, dated May 1, 2015 from International Application No. PCT/AU2015/050139, filed Mar. 31, 2015.

2nd International Written Opinion, dated Dec. 1, 2016 from International Application No. PCT/AU2015/050139, dated Mar. 31, 2015.

International Preliminary Report on Patentability, dated Feb. 20, 2017 from International Application No. PCT/AU2015/050139, dated Mar. 31, 2015.

* cited by examiner

Figure 12

- 1200
- 1210 → HOSPITAL / John Smith / Signout
- Sidebar (606): Home, Patient Details, Background, Documents, Radiology, Histology, Photos, Video, Decision, Report, Conference, Calendar, Participants
- Individual | Date of MDT Meeting 15|07|14
- Block Book? [Y][N]
- Surname [ ]   Speciality [ ] ← 1202
- First Name [ ]   Hospital [ ]
- Email [ ]   Telephone [ ]
- [MDT] [SMDT]   [Colorectal ▼]
- 608

Figure 13

- 1300
- 1310 → HOSPITAL / John Smith / Signout
- Sidebar (606): Home, Patient Details, Background, Documents, Radiology, Histology, Photos, Video, Decision, Report, Conference, Calendar, Participants
- Hospital | Date of MDT Meeting 15|07|14
- Block Book? [Y][N]
- Hospital [ ]   Speciality [ ] ← 1302
- Email [ ]   Telephone [ ]
- [MDT] [SMDT]   [Colorectal ▼]
- 608

ONLINE COLLABORATION SYSTEMS AND METHODS

CROSS-REFERENCE TO RELATED APPLICATIONS

The present application is a national phase entry under 35 U.S.C. § 371 of International Application No. PCT/AU2015/050139, filed on Mar. 31, 2015, published in English, which claims priority from Australian Patent Application No. 2015200410, filed Jan. 28, 2015, the disclosures of which are hereby incorporated herein by reference.

TECHNICAL FIELD

Described embodiments relate generally to online collaboration systems and methods. In particular, embodiments relate to server-hosted online collaboration environments to allow collaboration among multiple users. Such on-line collaboration environments are intended to allow conducting of online meetings. Some embodiments relate to server-hosted web portals to allow coordination, scheduling and/or controlling of online meetings conducted in such online collaboration environments.

BACKGROUND

Team meetings in disciplines, such as the medical, business, education and legal sectors, often involve a collaboration between a group of colleagues to consider a proposed course of action for managing a particular item or situation with a view to determining an agreed outcome and a conclusion of the meeting.

For example, in the medical section, multidisciplinary team (MDT) meetings ordinarily involve a group of specialists or experts in different fields of medicine and surgery coming together at regular intervals to discuss patient diagnosis, and in particular, patients with cancer, with a view to determining case-appropriate management options for patients. These management options may then be discussed with the patient and a treatment pathway may be agreed upon.

MDT meetings form an important part of cancer care and seek to ensure that patients with potential or confirmed cancers are offered treatments in line with nationally and/or internationally recognised guidelines. For example, the National Cancer Peer Review Programme and National Institute of Clinical Excellences (NICE) have issued recommendations, "Improving Outcomes Guidance (JOG)", detailing how MST forms part of such care.

It is desired to address or ameliorate one or more shortcomings or disadvantages associated with existing methods or systems for conducting team meetings, or to at least provide a useful alternative thereto.

SUMMARY

Some embodiments relate to an online collaboration system comprising at least one server in communication with multiple client computing devices over a communication network, the at least one server executing program code to host an online collaborative environment in which users of the client computing devices can collaborate, wherein the at least one server executes program code to facilitate an online meeting between the users of the client computing devices in the online collaboration environment, display a plurality of conference panels on a user interface of at least some of the multiple client computing devices, each conference panel configured to depict a real-time video stream associated with one of the client computing devices participating in the online meeting and display at least one display panel on the user interface of the at least some of the multiple client computing devices, wherein the at least one display panel of each user interface is configured to display common shared information relating to the online meeting.

In some embodiments, the at least one server may execute program code to provide at least one user selectable display option to allow display of information in the display panel. For example, the at least one user selectable display option to allow display of information in the display panel may allow selection of the information from a data record. The at least one server may execute program code to provide to the user interface of the at least some of the multiple client computing devices at least one user selectable display option to allow display of information in the display panel.

In some embodiments, the at least one server may execute program code to provide at least one user selectable control option to allow control of the user's participation in the online collaborative environment. For example, the at least one user selectable control option may comprise at least one of a video stream control option, an audio stream control option, a camera view control option and a mark-up tool control option. The at least one server may execute program code to provide to the user interface of the at least some of the multiple client computing devices the at least one user selectable control option to allow control of the user's participation in the online collaborative environment.

The at least one user selectable control option may comprise a media control option and in response to selection of the media control option, the at least one server may execute program code to control a broadcast of a media stream associated with the user to other client computing devices participating in the online collaborative environment. In some embodiments, the at least one server may execute program code to transmit a media control request to a video communications server to control the broadcast of the media stream, wherein video communications server may be configured to receive and relay media streams to and from the multiple client computing devices associated with an online meeting being held in the online collaborative environment.

In some embodiments, the at least one user selectable control option may comprise a mark-up tool control option and in response to selection of the mark-up tool control option, the at least one server may execute program code to display interactions of the user with the online collaborative environment in the online collaborative environment.

In some embodiments, the at least one server may execute program code to display a proposed course of action in a window of the online collaborative environment. For example, the at least one server may execute program code to display a proposed course of action in a window or panel on the user interface of the at least some of the multiple client computing devices. The at least one server may execute program code to provide at least one user selectable consent option to allow a user to submit an indication of agreement with the displayed proposed course of action. For example, the at least one server may execute program code to provide the at least one user selectable consent option to the user interface of the at least some of the multiple client computing devices. The at least one server may execute program code to provide, for example, to the user interface, at least one user selectable option to allow a secure record to be created, wherein the secure record may comprise a recording of at least a portion of an online meeting relating to the proposed course of action conducted in the online collaboration environment.

In some embodiments, the online meeting may be a multidisciplinary team meeting and at least some of the users may be specialists in different fields of medicine and/or surgery.

Some embodiments relate to a method of hosting an online collaborative environment in which users of client computing devices can collaborate, the method operable in an online collaboration system comprising at least one server in communication with multiple client computing devices over a communication network, the method comprising facilitating an online meeting between the users of the client computing devices in the online collaboration environment, displaying a plurality of conference panels on a user interface of at least some of the multiple client computing devices, each conference panel configured to depict a real-time video stream associated with one of the client computing devices participating in the online meeting and displaying at least one display panel on the user interface of the at least some of the multiple client computing devices, wherein the at least one display panel of each user interface is configured to display common shared information relating to the online meeting.

Some embodiments relate to a web portal system comprising at least one server in communication with multiple client computing devices over a communication network, the at least one server executing program code to provide a web portal for controlling user participation in an online collaborative environment being hosted by the at least one server, wherein the online collaborative environment allows users of the client computing devices to collaborate as participants, wherein the at least one server executes program code to provide at least one user selectable control option to allow a user to control at least one other user's participation in the online collaborative environment by controlling a broadcast of a media stream associated with the other user to the client computing devices. For example, the at least one server may execute program code to provide to a user interface of at least one of the multiple client computing devices the at least one user selectable control option to allow a user to control at least one other user's participation in the online collaborative environment.

In some embodiments, in response to selection of the at least one user selectable control, the at least one server may execute program code to cause a media stream control request to be transmitted to a video communications server to control the broadcast of the media stream, wherein the video communications server may be configured to receive and relay media streams to and from the multiple client computing devices associated with an online meeting being held in the online collaborative environment. For example, the media stream control request may comprise a stream identifier associated with the one other user's or participant's computing device.

In some embodiments, the at least one server may execute program code to provide at least one user selectable schedule option to allow a user to schedule an online meeting for the online collaborative environment. For example, the at least one server may execute program code to provide to the user interface of the at least one of the multiple client computing devices the at least one user selectable schedule option to allow a user to schedule an online meeting for the online collaborative environment. In response to selection of the at least one user selectable schedule option, the at least one server may execute program code to cooperate with a video communications server to enable the video communications server to receive and relay media streams to and from the multiple client computing devices associated with the online meeting. For example, the at least one server may execute program code to cooperate with a video communications server to determine a meeting session identifier for the schedule online meeting. The at least one server may execute program code to provide the client computing devices associated with the online meeting with the meeting session identifier to enable the client computing devices to subscribe to the video communications server to receive media streams associated with the meeting session identifier.

In some embodiments, the at least one server may execute program code to provide, for example, to the user interface, at least one user selectable option to allow a user to create a data record for recording data associated with the online meeting, wherein the data record may be remotely located from the client computing device associated with the user. The at least one server may execute program code to provide, for example, to the user interface, at least one user selectable option to allow a user to add data to the data record, wherein the data may comprise at least one of a media file, a document and/or a link to a media file or document.

In some embodiments, the at least one server may execute program code to provide, for example, to the user interface, at least one user selectable option to allow a user to add data to the data record, wherein the data may comprise a recording of at least a portion of an online meeting conducted in the online collaboration environment.

In some embodiments, the at least one server may execute program code to provide, for example, to the user interface, at least one user selectable invite option to invite users of the client computing devices to collaborate as participants in the online meeting, wherein the user selectable invite option may identify a client computing device, and in response to selection of the at least one user selectable invite option, the at least one server may execute program code to transmit an invitation to the identified client computing device.

Some embodiments relate to a method of controlling user participation in an online collaborative environment, the method operable in an web portal system comprising the at least one server in communication with multiple client computing devices over a communication network, wherein the online collaborative environment is arranged to be hosted by the at least one server and allows users of the client computing devices to collaborate as participants, the method comprising providing at least one user selectable control option to allow a user to control at least one other user's participation in the online collaborative environment by controlling a broadcast of a media stream associated with the other user to the client computing devices. For example, the method may comprise providing the at least one user selectable control option to a user interface of at least one of the multiple client computing devices.

Some embodiments relate to an online collaboration system comprising at least one server in communication with multiple client computing devices over a communication network, the at least one server executing program code to host an online collaborative environment in which users of the client computing devices can collaborate, wherein the at least one server executes program code to facilitate a real-time multimedia meeting between the users of the client computing devices in the online collaboration environment to allow discussion of a proposed course of action and determination of an agreed outcome.

Some embodiments relate to method of hosting an online collaborative environment in which users of client computing devices can collaborate, the method operable in an online collaboration system comprising at least one server in communication with multiple client computing devices over a communication network, the method comprising facilitating a real-time multimedia meeting between the users of the client computing devices in the online collaboration environment to allow discussion of a proposed course of action and determination of an agreed outcome.

Some embodiments relate to a computer program product comprising a computer readable medium encoded with computer executable instructions, which when executed in a computer system, is effective to cause the computer system to carry out any of the above described methods. In some embodiments, the computer readable medium may be a non-transitory computer readable medium.

Some embodiments relate to a system comprising the online collaboration system described above and a video communications server.

BRIEF DESCRIPTION OF DRAWINGS

Embodiments are described in further detail below, by way of example and with reference to the accompanying drawings, in which:

FIGS. 6 to 16 show example displays of a web portal for coordinating an online meeting shown on a user interface of one of the computing devices of FIG. 1, according to some embodiments;

DESCRIPTION OF EMBODIMENTS

Described embodiments relate generally to online collaboration systems and methods. In particular, embodiments relate to server-hosted online collaboration environments to allow collaboration among multiple users. Such online collaboration environments are intended to allow conducting of online meetings. Some embodiments relate to server-hosted web portals to allow coordination, scheduling and/or controlling of online meetings to be or being conducted in such online collaboration environments.

Some embodiments relate to online collaboration environments for conducting online meetings, such as real-time multimedia meetings, involving a collaboration between a group of participants or colleagues to consider a course of action for managing a particular item or situation with a view to determining an agreed outcome or consensus. Some embodiments relate to a web portal to allow a user of the web portal, such as a coordinator of an online meeting, to schedule a meeting and to prepare and collate information pertaining to the scheduled meeting, at least some of which may be accessed through the online collaboration environment during the meeting. For example, a user may determine a proposed course of action for managing a particular item and/or situation which may be presented during the scheduled meeting as a proposal for consideration. The web portal may also be employed by a user, such as the coordinator of the online meeting, to manage and control the online meeting. For example, the web portal may provide controls to allow an authorised user to control another user's level of participation in the online collaborative environment by controlling a broadcast of that user's video and/or audio streams to other participants in the online meeting.

In some embodiments, the online meetings may be team meetings relating to the medical, business, education and/or legal sector. For example, in some embodiments the online meetings may be multidisciplinary team meetings.

Figure 1:
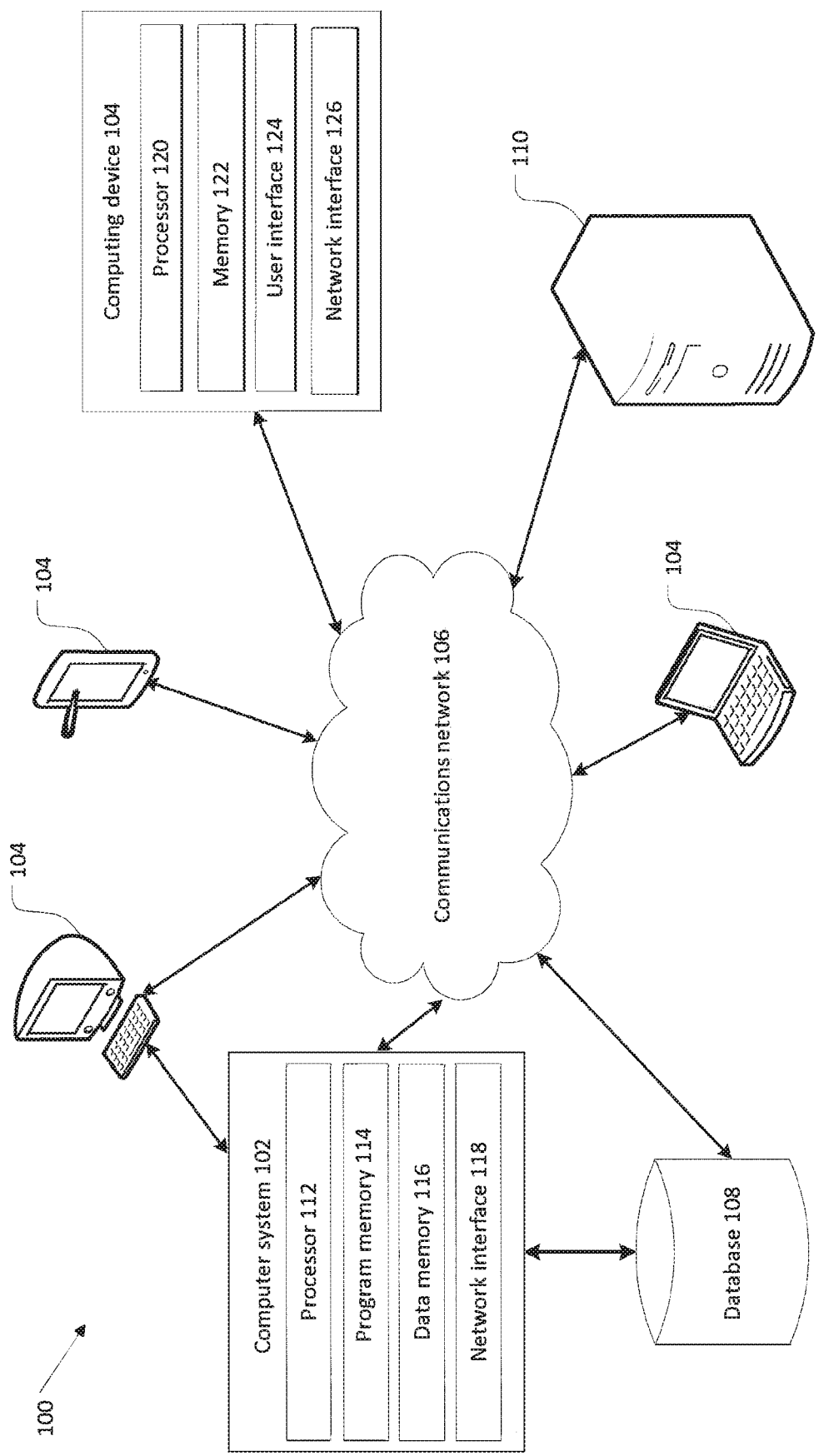
FIG. 1 is a block diagram of an example of a communications system for conducting and/or coordinating online meetings comprising a computer system and a plurality of computing devices, according to some embodiments.

Referring to FIG. 1, there is illustrated an example of a communications system 100 comprising a computer system 102 in communication with a plurality of computing devices 104 across a communications network 106, such as a local area network, a wireless data network, an intranet or the Internet or a combination of a number of such networks.

The computer system 102 comprises a processor 112 (which may include multiple processing components or multiple virtual or physical servers operating together), program memory 114, data memory 116 and a network interface 118.

The processor 112 may include components such as digital signal processing units (DSPUs), central processing units (CPUs), arithmetic logic units (ALUs) and registers for storing data.

Program memory 114 and/or data memory 116 may comprise a combination of volatile and non-volatile computer readable storage. For example, program memory 114 may include read-only memory (ROM) such as erasable ROM (EROM) and electrically erasable programmable ROM (EEPROM or flash ROM), or random access memory (RAM) such as static RAM (SRAM), dynamic RAM (DRAM) or non-volatile RAM (NVRAM or flash). Program memory 114 has sufficient capacity to store program code executable by the processor 112 in order to perform appropriate processing functions as described herein, including providing an online collaboration environment for facilitating the conducting of online meetings and providing a web portal for facilitating the scheduling and/or coordinating of online meetings in such online collaboration environments.

Data memory 116 may be configured to store data pertinent to operations of the computer system 102 and provision of service to the computing devices 104, and/or to store information pertaining to meetings, for example, data records, content such as video, audio, image, and/or text and contact details of potential participants.

The network interface 118 may comprise suitable hardware and software interfaces to facilitate wireless communication with computing devices 104, database 108, and/or video communications server 110, for example, over a network, such as communications network 106, which may comprise a local area network, a wireless data network, an intranet or the Internet or a combination of a number of such networks. For example, the network interface 118 may comprise a USB port, Ethernet port, a wireless adapter or a Bluetooth module. In some embodiments, the network interface 118 may comprise suitable hardware and software interfaces to facilitate wired communication between the computer system 102, computing devices 104, database 108 and/or video communications server 110.

In some embodiments, the computer system 102 may comprise a PC, server or server system, smartphone, tablet, laptop and may, in some embodiments, comprise multiple computer devices, servers or server systems.

The computing device(s) 104 comprises at least one processor 120, one or more forms of memory 122, a user interface 124 and a network interface 126.

Memory 122 may comprise volatile (e.g. RAM) and non-volatile (e.g. hard disk drive, solid state drive, flash memory and/or optical disc) storage. For example, memory 122 may store or be configured to store a number of software applications or applets executable by the at least one processor 120 to perform various device-related functions discussed herein.

The user interface 124 may comprise at least one output device, such as a display and/or speaker, for providing an output for the computing device 104 and at least one input device, such as a touch-screen, a keyboard, mouse, microphone, video camera, stylus, push button, switch or other peripheral device that can be used for providing user input to the computing device 104. In some embodiments, the user interface 124 comprises a display, a speaker, a microphone, and a video camera.

The network interface 126 may comprise suitable hardware and software interfaces to facilitate wireless communication with the computer system 102, other computing devices 104, database 108 and/or video communications server 110, for example, over a network, such as communications network 106, which may comprise a local area network, a wireless data network, an intranet or the Internet or a combination of a number of such networks. For example, the network interface 126 may comprise a USB port, Ethernet port, a wireless adapter or a Bluetooth module. In some embodiments, the network interface 126 may comprise suitable hardware and software interfaces to facilitate wired communication between the computer device 104, the computer system 102, other computing devices 104, database 108 and/or video communications server 110.

In some embodiments, the computing device 104 may comprise a mobile or hand-held computing device such as a smartphone or tablet, a laptop, or PC, and may, in some embodiments, comprise multiple computer devices.

In some embodiments, the communications system 100 comprises a client-server architecture where the computer system 102 is configured as a server and at least one of the computing devices 104 is configured as a client computing device.

The communications system 100 may further comprise a database or content file server 108 for storage and retrieval of data. The database 108 may be coupled to and accessible by the computer system 102, for example, directly or via a private communications network. In some embodiments, the database 108 may be coupled to and accessible by the computer system 102 and/or the computing device 104 over the communications network 106. The database 108 may be configured to store data pertinent to operations of the computer system 102 and provision of service to the computing devices 104. For example, the database 108 may store information pertinent to meetings including content such as data records, content including video, audio, image and/or text relating to the meetings and/or contact details of potential participants.

The communications system 100 comprises a video communication server (VCS) 110 configured to execute code to facilitate sharing of audio/video content or streams between the computing devices 104 participating in online meetings. In some embodiments, the computer system 102 comprises the VCS 110 and in other embodiments, the VCS 110 is located remotely from the computer system 102. The VCS 110 is configured to communicate with the computer system 102, computing devices 104 and/or the database 108 across the communications network 106. In some embodiments, the VCS 110 is configured to receive streams from one or more of the computing devices 104, assign a session ID to the streams and to relay the streams to other computing devices 104 participating in an online meeting, as will be discussed in more detail below. In some embodiments, the VCS 110 comprises a real-time communication web service, such as OpenTok® to cooperate with software applications or applets of the computing devices 102 to provide for real-time communications between computing devices 104 participating in online meetings in the online collaboration environment.

Figure 2:
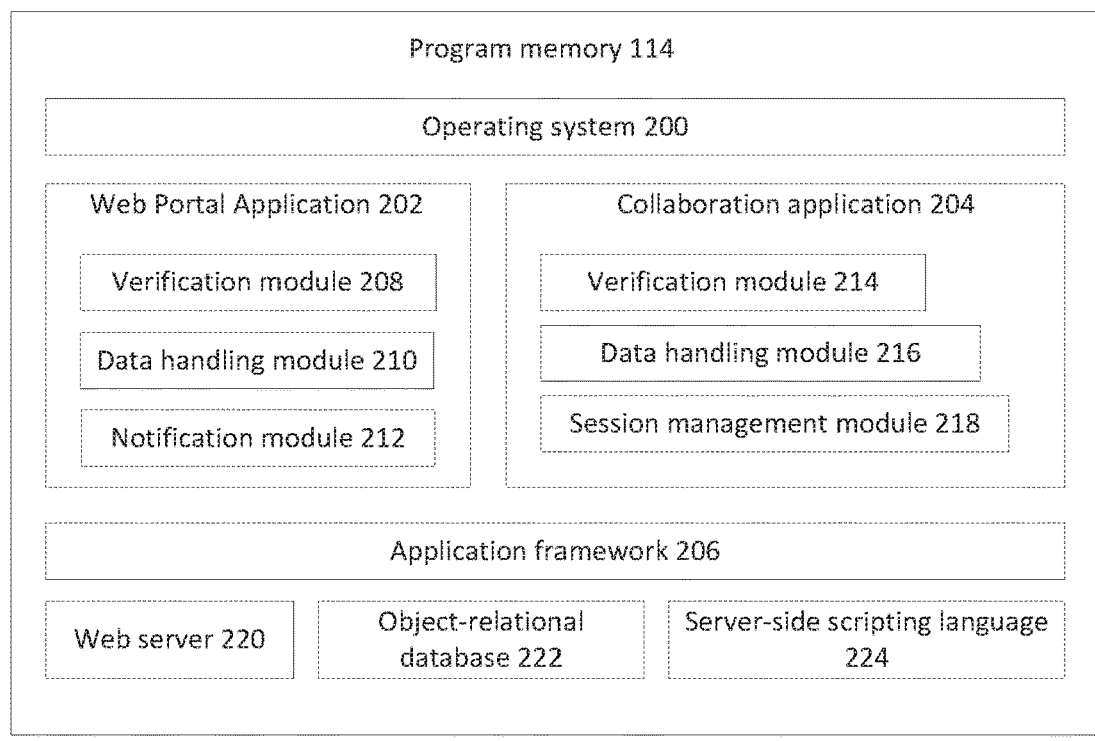
FIG. 2 is a block diagram depicting program memory of the computer system of FIG. 1.

Referring to FIG. 2, there is shown a block diagram of program memory 114 of the computer system 102. Program memory 114 comprises program code including an operating system 200, and a web portal application 202 and a collaboration application 204, supported by suitable application framework 206, such as Symfony (for PHP).

The web portal application 202 comprises program code, such as executable code modules, which, when aggregated and executed by the one or more processors 112, perform programmed functions as described herein and cause the computer system 102 to act as a web portal system and to host a web portal for coordinating, scheduling and/or controlling online meetings, as will be discussed in more detail with reference to FIGS. 4 to 16. Such code modules include a verification module 208, a data handling module 210 and a notification module 212, for example.

The collaboration application 204 comprises program code, such as executable code modules, which, when aggregated and executed by the one or more processors 112, perform programmed functions as described herein and cause the computer system 102 to act as an online collaboration system and to host an online collaboration environment for conducting online meetings, as will be discussed in more detail with reference to FIGS. 17 to 23. Such code modules include a verification module 214, a data handling module 216 and a session management module 218, for example.

Program memory 114 may also comprise web server functions 220 (e.g. using a hypertext transfer protocol daemon (HTTP)), data processing functions and data storage and retrieval functions (e.g. using structured query language (SQL) support, such as object-relational database 222) in conjunction with database 108. Program memory 114 may also comprise scripting language support 224, such as Microsoft™ ASP, ASP.NET, Java/J2EE or PHP.

Figure 3:
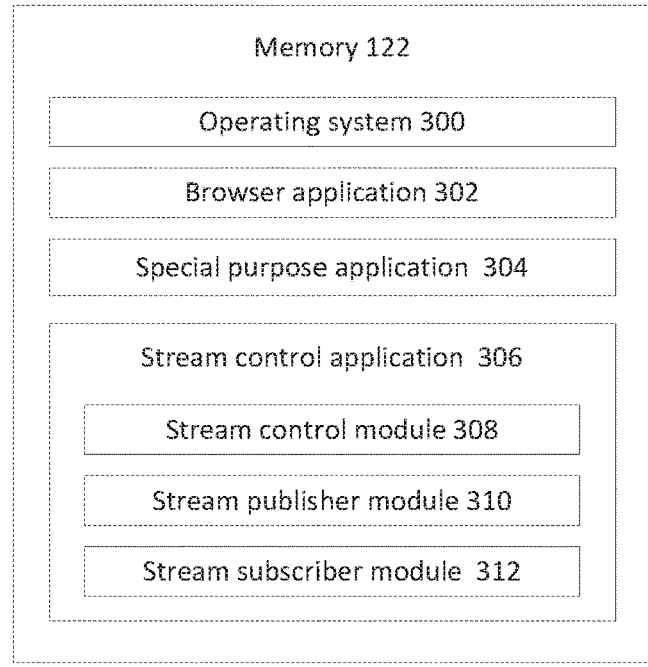
FIG. 3 is a block diagram depicting memory of one of the computing devices of FIG. 1.

When supported by and combined with the application framework 206, and the other server-side functions described previously, the web portal application 202 provides a web portal and the collaboration application 204 provides an online collaboration environment. In some embodiments, the web portal and the online collaboration environment may encompass activities that can be viewed as being performed or executed at the computing devices 104. However, it is to be emphasised that the activities performed or executed at the computing devices 104 are reliant on program code (including applets, where appropriate) served by computer system 102 to the computing devices 104 and executed by a browser application 302 (FIG. 3). The functionality of the web portal and the online collaboration environment is therefore driven by code executed and served by the computer system 102.

Referring to FIG. 3, there is shown a block diagram of memory 122 of the computing device 104. Memory 122 includes an operating system 300 and a number of software applications or applets executable by the at least one processor 120 to perform various device-related functions.

At least one such software application includes a browser application 302 for enabling a user to navigate to sites accessible over the communications network 106 to receive content therefrom. In some examples, the browser application 302 can be used to communicate with computer system 102 to request content therefrom, in the form of one or more web pages provided as program code to the browser application 302 and executable by the processor 120. According to some embodiments, the computer system 102 is configured to serve code to the computing device 104 to provide a web portal generated by browser application 302 and viewable on a display of the user interface 124. Thus, the computer system 102 can be considered to act as a system for enabling or facilitating the scheduling and/or coordinating of online meetings or to act as a host for such a system. According to some embodiments, the computer system 102 is configured to serve code to the computing device 104 to provide an online collaboration environment generated by browser application 302 and viewable on a display of the user interface 124. Thus, the computer system 102 can be considered to act as an online collaboration system for enabling or facilitating the conducting of online meetings or to act as a host for such a system.

In some embodiments, the browser application 302 may be supplemented by a special-purpose add-on or may be substituted by special-purpose client software (i.e. an "app" for a smartphone or tablet device) in order to perform the functions described herein or to facilitate such functions. For example, for a computing device 104, a special purpose application 304 may be downloaded from the computer system 102 or a separate dedicated download server (not shown) and installed on the computing device 104. When such a special purpose application 304 is executing on the mobile client computing devices 104, it may facilitate appropriate formatting, interaction, display and input to enable the user interface functionality described herein. In this way, the special-purpose application 304 cooperates with the computer system 102 to provide access to and interaction with the web portal realised by the web portal application 202 implemented by the computer system 102 and the online collaboration environment realised by the collaboration application 204 implemented by the computer system 102.

For simplicity of illustration, the computer system 102 is generally described as serving code or one or more applets to the computing devices 104 to perform some of the described user interface functions. However, it should be understood that this includes the computer system 102 transmitting code and/or data to (and receiving code and/or data from) the special-purpose application 304 executing on the computing device 104 to enable that special-purpose application 304 to provide the necessary or appropriate displays and interactive features (e.g. display of information fields, user selectable options, conference panels etc.) described herein.

Memory 122 further comprises a stream control application 306 to set up and control transmissions of local video and/or audio streams from the user interface 124 of the computing device 104 to the VCS 110 and the receiving of video and/or audio streams from the VCS 110. The stream control application 306 may cooperate with the browser application 302 to allow the browser application 302 to output the received streams to the user interface 124. The stream control application 306 may also cooperate with the browser application 302 to allow the browser application 302 to output local video and/or audio streams to the user interface 124. In some embodiments, the stream control application 306 comprises a steam controller module 308, a stream publisher module 310 and a stream subscriber module 312, to perform or facilitate the functions described herein in connection with the management of video and/or audio streams. For example, the stream control application 306 may comprise Web RTC and OpenTok® software to cooperate with an OpenTok® web service provided by the VCS 110. Other client software applications may execute on the computing device(s) 104 using the operating system 300.

Figure 4:
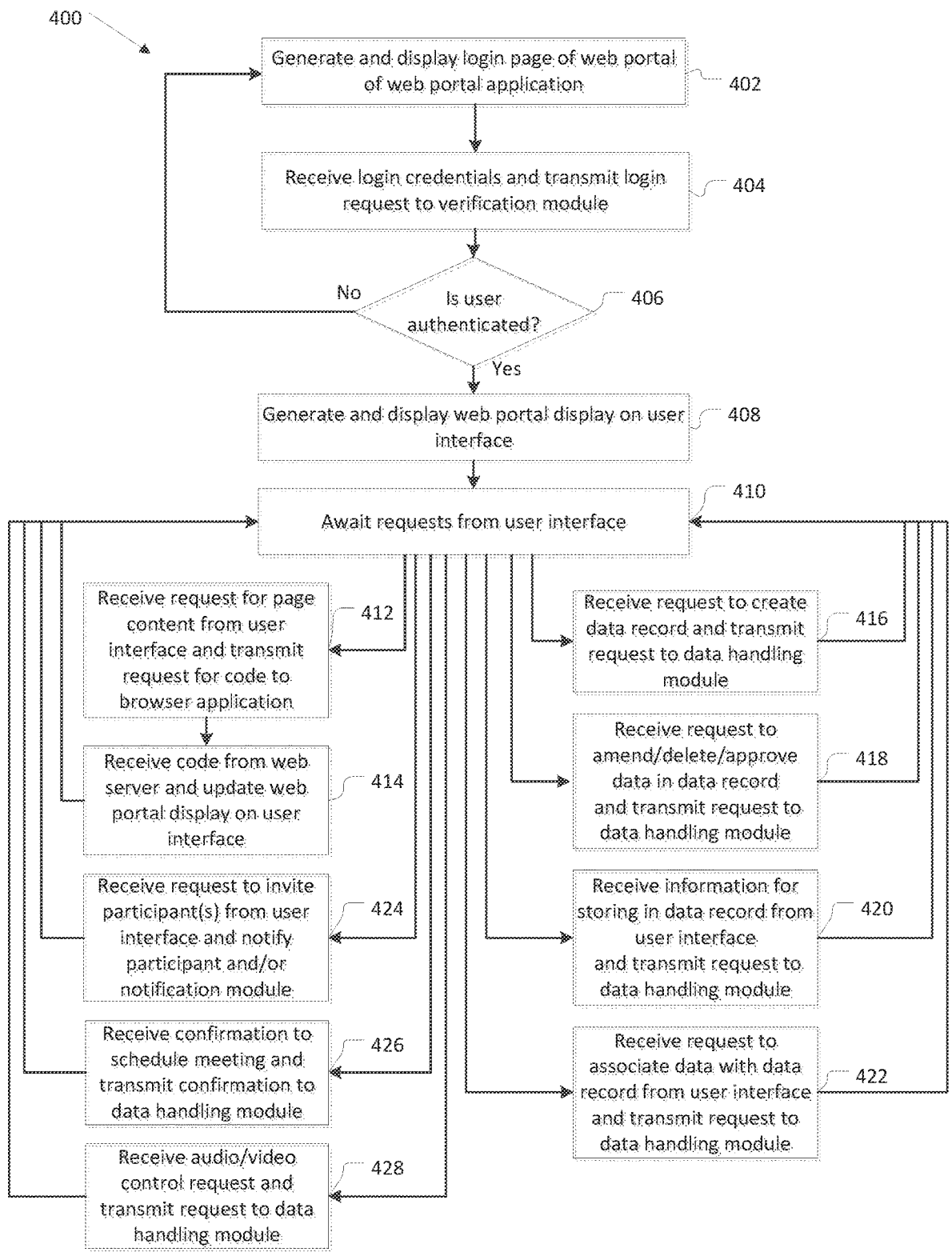
FIG. 4 is a process flow diagram depicting a method of coordinating, scheduling or controlling, an online meeting facilitated by a web portal application hosted on the computer system of FIG. 1, the method implementable by at least one of the computing devices of FIG. 1, according to some embodiments.

FIG. 4 is a process flow diagram of a method 400 of coordinating, scheduling and/or controlling an online meeting, operable on one of the computing devices 104 of the communications system 100, according to some embodiments. In particular, the method 400 is facilitated by the computer system 102 based on code served by the computer system 102 to one or more of the computing devices 104. Therefore, the acts described in relation to the method 400 are performed by execution in browser application 302 of browser-executable code served to the computing device 104 by the computer system 102.

Figure 5:
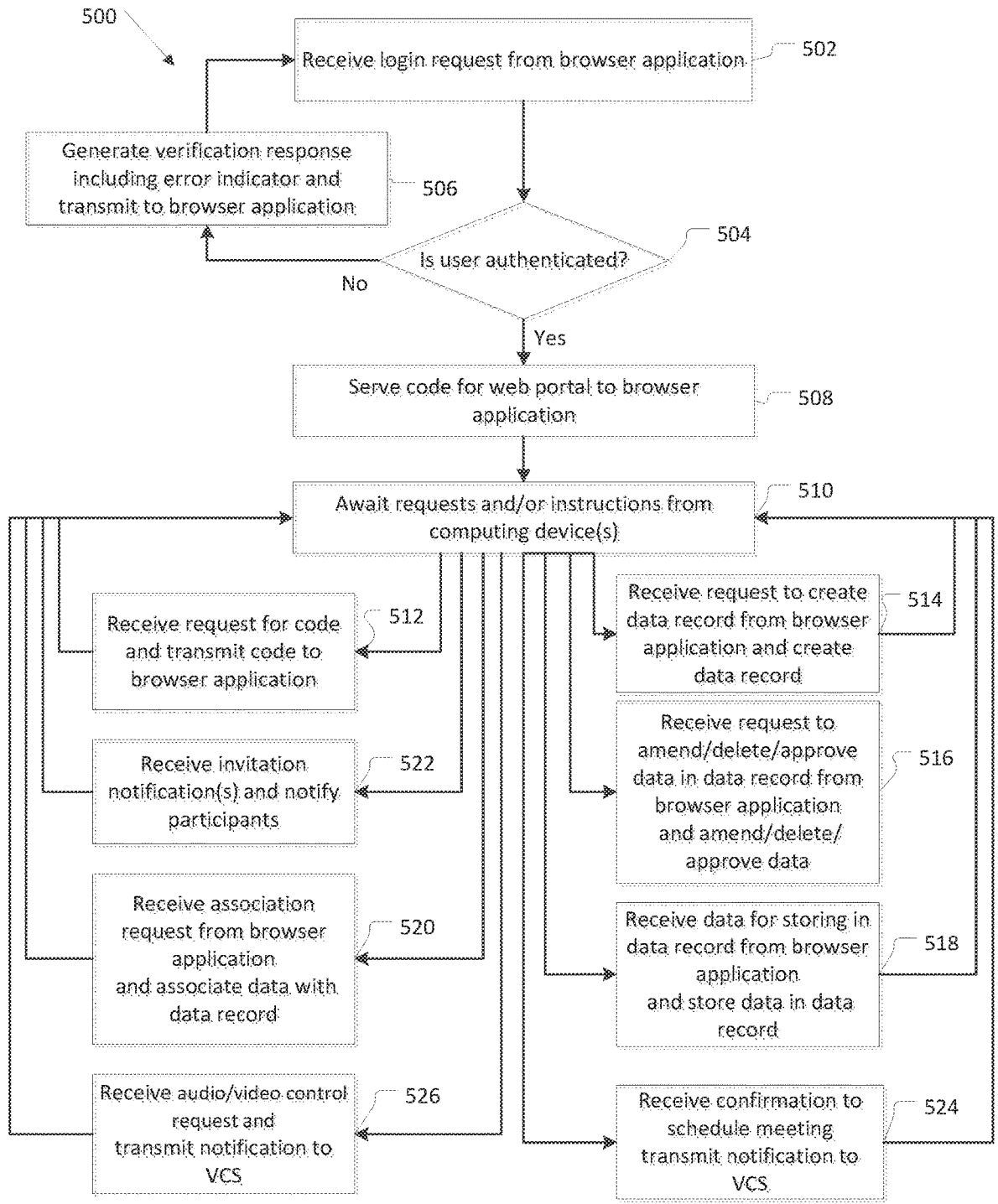
FIG. 5 is a process flow diagram depicting a method of coordinating, scheduling or controlling, an online meeting facilitated by a web portal application hosted on the computer system of FIG. 1, the method implementable by the computer system of FIG. 1, according to some embodiments.

FIG. 5 is a process flow diagram of a method 500 of coordinating, scheduling and/or controlling an online meeting, operable on the computer system 102 of the communications system 100, according to some embodiments.

The methods 400 and 500 are described with reference to FIGS. 6 to 16, which show exemplary web portal displays 600, 700, 800, 900, 1000, 1100, 1200, 1300, 1400, 1500, 1600 of a web portal or webpage viewable on the user interface 124 of the computing device 104, according to some embodiments. The web portal displays 600, 700, 800, 900, 1000, 1100, 1200, 1300, 1400, 1500, 1600 are generated by the browser application 302 in response to code served by the computer system 102 in accordance with the web portal application 202. Although the web portal displays 600, 700, 800, 900, 1000, 1100, 1200, 1300, 1400, 1500, 1600 relate specifically to web portal displays for an online meeting for use in the medical sector, for example, such as an online multidisciplinary team meeting, it will be appreciated that web portal displays appropriate for online meetings for other sectors may be generated by the browser application 302 in response to code served by the computer system 102 in accordance with the web portal application 202.

Referring to FIG. 4, the method 400 beings with the browser application 302 generating a login page of a web portal of the coordinator web portal application 202 for display on the user interface 124, at 402. In some embodiments, a user is provided with sign-in details or credentials, for example, a username and password, which may be employed to securely access the web portal application 202 for scheduling and/or coordinating online meetings. Forgotten or misplaced usernames and passwords may be recovered for a user using details provided during a signup process.

In some embodiments, the browser application 302 receives login credentials via the login page of the web portal which triggers the processor 120 of the computing device 104 to execute code of the browser application 302 to cause a login request to be transmitted to the computer system 102 for verification, at 404.

Referring to FIG. 5, the computer system 102 receives the login request, at 502, which triggers the processor 112 of the computer system 102 to execute the verification module 208 of the web portal application 202 to cause the computer system 102 to determine whether or not the credentials are valid and whether the user is authorised to access the web portal application 202, at 504. For example, the computer system 102 may be configured to compare the credentials submitted by the user with authorised coordinator details stored locally in data memory 116 or at database 108.

If the verification module 208 deems that the user is unauthorised, the verification module 208 may cause a verification response including an error indicator to be transmitted to the browser application 302, at 506.

Referring to FIG. 4, when the computing device 104 receives a verification response including the error indicator, the browser application 302 may be caused to regenerate and display the login page to provide a user with another opportunity to re-enter the login details, at 402 and may, for example, and display an error message on the user interface 124 of the computing device 104.

Referring to FIG. 5, if the verification module 208 deems the user authorised, the web server 220 causes the computer system 102 to serve code, such as HTML text for the web portal, to the browser application 302 of the computing device 104 to cause the browser application 302 to show a web portal display 600, 700, 800, 900, 1000, 1100, 1200, 1300, 1400, 1500, 1600 on the user interface 124, at 508. In some embodiments, the verification module 208 may also cause a verification response including an authorisation indicator to be transmitted to the browser application 302. The computer system 102 may then await further requests and/or instructions from the computing devices 104, at 510.

Referring again to FIG. 4, receipt of code, such as HTML text for the web portal, from the web server 220 causes the browser application 302 to show a web portal display 600, 700, 800, 900, 1000, 1100, 1200, 1300, 1400, 1500, 1600 on the user interface 124, at 408, to allow user to coordinate, schedule and/or control online meetings for the online collaboration environment. The computing device 104 may then await further requests and/or instructions from the user interface 124 of the computing device, at 410.

Figure 6:
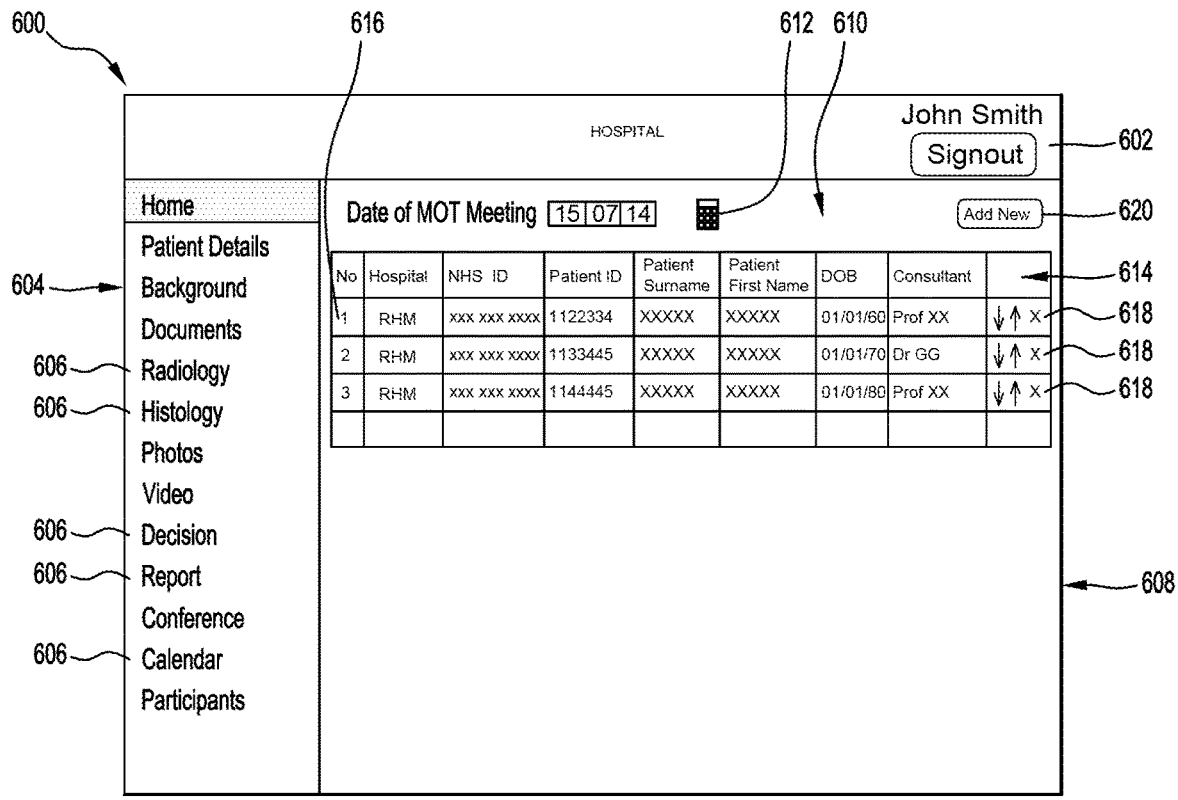

As depicted in FIG. 6, web portal display 600 shows a user-specific information section 602, which displays user details, for example, the user's name and a sign-out selectable option to allow the user to sign-out or securely exit the web portal.

The web portal display 600 shows a tab 604 providing a list of topic options 606 relating to information associated with a patient's case, for example, patient details, background, documents, radiology, histology, photos, video, decision, report, conference, calendar and participants. However, it will be understood that in some embodiments, the tab 604 may provide only a subset of these topic options 606 and/or may provide additional topic options 606. The topic options 606 may relate to information pertinent to the online meeting being conducted in the online collaboration environment. For example, in the event that the online meeting relates to a business meeting, the topic options may reflect information topics relevant to the business meeting.

The list of topic options 606 may be user selectable topic options 606. In some embodiments, selection of a topic options 606 triggers code of the browser application 302 being executed by the processor 120 to request further page code from the web server 220, at 412, as shown in FIG. 4. As depicted in FIG. 5, in response to receiving the request for code, the web server 220 transmits or serves the code to the browser application 302, at 512, and the method reverts to 510 awaiting further requests or instructions from the computing device (s) 204, at 510.

Referring again to FIG. 4, the browser application 302 receives the code from the web server 220 and the processor 120 executes the code to cause the browser application 302 to display information associated with the selected topic option 606, at 414 and the method reverts to 410 awaiting further requests or instructions from the user interface 224, at 410. In some embodiments, selection of a topic options 606 triggers code of the browser application 302 being executed by the processor 120 to execute an applet within the code of the browser application 302 to display information associated with the selected topic option 606.

The web portal display 600 shows a display window 608 for displaying information relating to a topic of the topic options 606. When the home topic option 606 of the tab 602 is highlighted or selected, as is the case in FIG. 6, the display window 608 depicts an information screen 610 showing a user selectable calendar option 612 to allow a user to select a particular date which is indicated in the display window 608. In response to the selection of a particular calendar date by a user, a set of cases 614 which have been scheduled for that date are presented in the display window 608. For example, selection of a particular calendar date triggers code of the browser application 302 being executed by the processor 120 to request further page code from the web server 220 so that the requested information may be displayed, 412, 414 and in response to receiving the request for code, the web server 220 serves the code to the browser application, at 512.

The set of cases 614 comprises a list of case items 616, and each item 616 may detail particulars of the case, for example, the patient's name, date of birth, patient number, NHS number, the hospital responsible for the patient and the consultant responsible for the patient. Each case item 616 may be associated with a corresponding data record which may be stored at database 108 and/or in data memory 116 of the computer system 102. The case items 616 may relate to cases pertinent to the online meeting being conducted in the online collaboration environment. For example, in the event that the online meeting relates to a business meeting, the case items 616 may detail particulars of the case such as a project title, reference number, project manager, and/or due date for completion.

Each case item 616 may include a user selectable modification option 618 to allow the user to reorder the case within the set of cases 614, for example, by selecting either of an up or down arrow option, and to delete the case, for example, by selecting the X option. In some embodiment, selection of a user selectable modification option 618 triggers code of the browser application 302 being executed by the processor 120 to request further page code from the web server 220, at 412, as shown in FIG. 4. As depicted in FIG. 5, in response to receiving the request for code, the web server 220 transmits or serves the code to the browser application 302, at 512, and the method reverts to 510 awaiting further requests or instructions from the computing device (s) 204, at 510. Referring again to FIG. 4, the browser application 302 receives the code from the web server 220 and the processor 120 executes the code to cause the browser application 302 to display information associated with the selected topic option 606, at 414. In other embodiments, selection of a user selectable modification option 618 triggers code of the browser application 302 being executed by the processor 120 to execute an applet within the code of the browser application 302 to display information associated with the selected modification option 518 and/or addition option 620.

The information screen 510 may also depict a user selectable addition option 620 to allow a user to add a new case item 616 to the set of cases 614 for the identified date. In some embodiments, as depicted in FIG. 4, selection of a user selectable addition option 620 triggers code of the browser application 302 being executed by the processor 120 to transmit a request to create a new data record to the data handling module 210 of the web portal application 202 deployed on the computer system 102, at 416. Referring to FIG. 5, the data handling module 210 of the web portal application 202 receives the request from the browser application 302 and creates a new data record for the new case item 616 in the database 108 and/or data memory 128, at 514. Thus, the browser application 302 is responsive to receipt of a request to add a new case item to the web portal application to transmit a request to the data handling module 210 to cause the creation of a new data record for the case item.

The user may select the patient details topic option 606 from the tab 602 to cause the automatic loading of the information associated with the patient details topic option 606 for display in the display window 608. In some embodiments, once the user selects the user selectable addition option 620, the patient details topic option 606 of the tab 604 automatically becomes highlighted or otherwise visually identified and information associated with the patient details topic option 606 is automatically displayed in the display window 608, as depicted in FIG. 7.

Referring again to FIG. 4, the user interacts with the web portal displays 700, 800, 900, 1000, shown on the user interface 124 to cause case information pertaining to an online meeting to be scheduled to be submitted to the web portal application 202 and associated with the case item 616, at 420 and associated with the data record.

Figure 7:
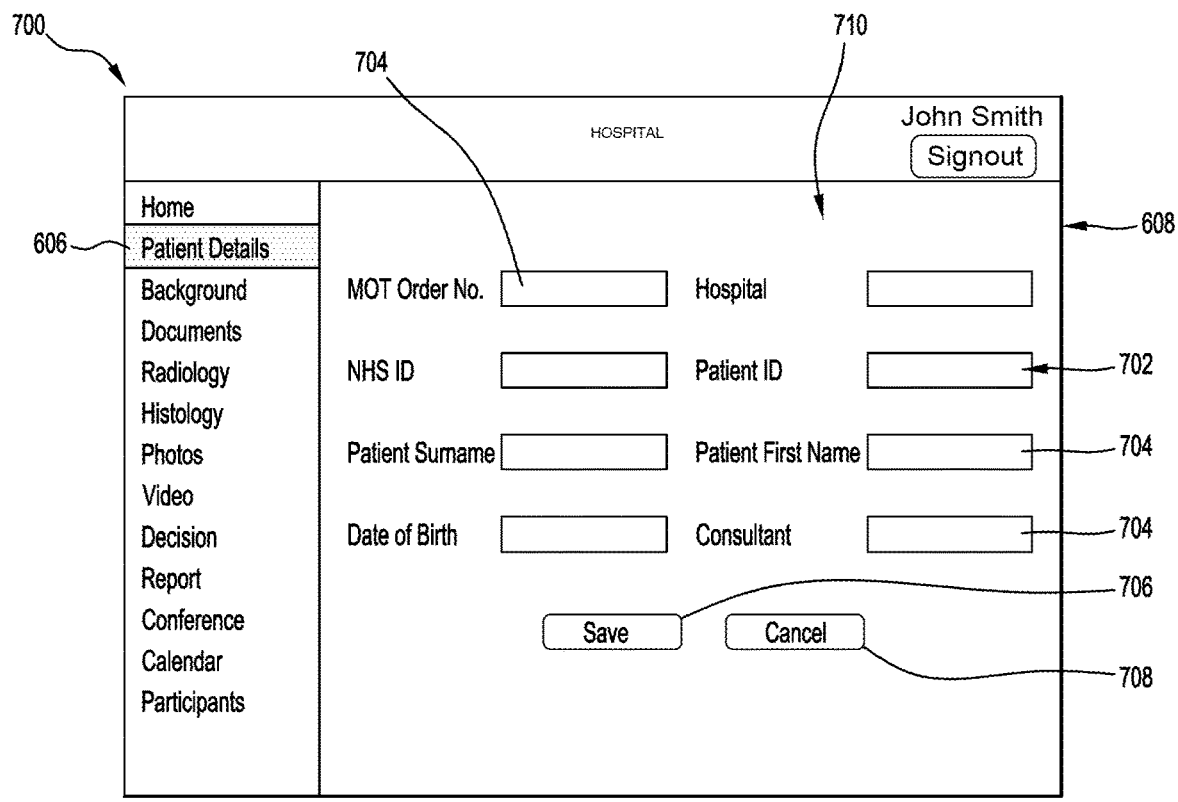

As depicted in FIG. 7, an information screen 710 associated with the patient details topic option 606 displayed in the display window 608 comprises a patient information form 702 comprising a plurality of information fields 704 or text boxes for receiving information detailing particulars of the case. The information fields 704 are arranged to receive text inputted by the user via the user interface 124 of the computing device 104. The patient information form 702 provides a user selectable save option 706 to allow the information inserted into the information fields 704 to be saved as a new case item 616. For example, as illustrated in FIG. 4, when information or data inputted into the information fields 704, selection of the save option 706 triggers code of the browser application 302 being executed by the processor 120 to transmit the information to the data handling module 210 of the web portal application 202, at 420. As shown in FIG. 5, in response to receiving the information from browser application 302, the data handling module 210 being executed by the processor 112 may cause the computer system 102 to store the information in the data record associated with the case item 616, at 518. In some embodiments, the data handling module 210 may pass details of the information to the web server 220 for updating page code associated with web portal display 600 of the home topic option 606 for a particular calendar date as shown in FIG. 6.

The user may select the background topic option 606 from the tab 602 to cause the automatic loading of information associated with the background topic option 606 and the display of the information screen 612 in the display window 608. In some embodiments, selection of the save option 706 causes automatic highlighting or otherwise visual identification of the background topic option 606 and the automatic display of information associated with the background topic option 606 in the display window 608, as depicted in FIG. 8.

The patient information form 702 also provides a user selectable cancel option 708 to cancel or delete the information inserted into the information fields 704 and/or to revert to the home topic option 606 and associated display window 608, as depicted in FIG. 6. In some embodiments, selection of the cancel option 708 triggers code of the browser application 302 to transmit a cancel or delete request to the data handling module 210 of the web portal application 202, at 418, as shown in FIG. 4. Referring to FIG. 5, in response to receiving the cancel or delete request, the data handling module 210 may delete the information associated with the delete request from the data record associated with the case item 616, at 516. In some embodiments, the data handling module 210 may pass details of delete request to the web server 220 to cause the web server 220 to update page code associated with the web portal display 600 of the home topic option 606 for a particular calendar date as shown in FIG. 6.

Figure 8:
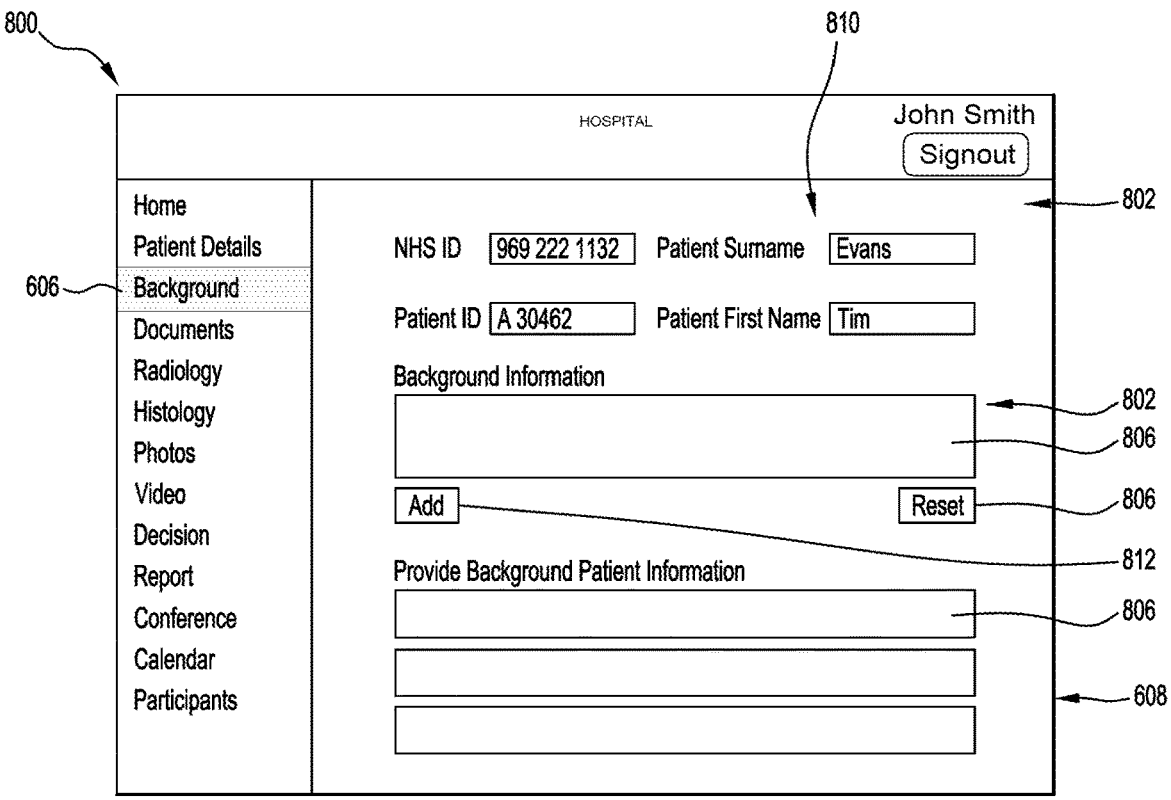

As depicted in FIG. 8, an information screen 810 associated with the background topic option 606 displayed in the display window 608 comprises a patient identification section 802 providing details identifying the patient, including the patient's name and identification, and a background information form 804 comprising a background information field 806, such as a text box, for receiving background information relating to the case and/or patient and a previous background patient information field 808, such as a text box, for receiving previous background information relating to the patient. The information fields 806, 808 are arranged to receive text inputted by the user via the user interface 124 of the computing device 104. The background information form 804 depicts a user selectable add option 812 to allow the information inserted into the information fields 806, 808 to be saved in connection with the case item 516. In some embodiments, insertion of text into the information fields 806, 808 and selection of the add option 812 by the user triggers code of the browser application 302 being executed by the processor 120 to transmit the inputted information to the data handling module 210 of the web portal application 202, at 420, as shown in FIG. 4. Referring to FIG. 5, in response to receiving the information, the data handling module 210 may cause the information to be stored in the data record associated with the case item 616, at 518.

The user may select the documents topic option 606 from the tab 602 to cause the automatic loading of the information screen 910 associated with the documents topic option 606 for display in the display window 608. In some embodiments, selection of the user selectable add option 810 causes automatic highlighting or otherwise visually identifying of the documents option 606 and the automatic display of an information screen 910 associated with the documents option 606 in the display window 608, as depicted in FIG. 9.

The background information form 804 also depicts a user selectable reset option 814 to cancel or delete the information inserted into the information fields 806, 808 and/or to revert to a previous topic option 606, such as the home topic option or the patient details topic option and the associated information screen 600, 700, as depicted in FIG. 6 or 7, respectively. In some embodiments, selection of the reset option 814 triggers code of the browser application 302 to transmit a cancel or delete request to the data handling module 210 of the web portal application 202, at 418, shown in FIG. 4. Referring to FIG. 5, in response to receiving the cancel or delete request, the data handling module 210 may delete the information in the data record associated with the case item 616, at 516. In some embodiments, the data handling module 210 may pass details of the cancel or delete request to the web server 220 for updating page code associated with web portal display 800 of the home topic option 606 for a particular calendar date as shown in FIG. 6.

Figure 9:
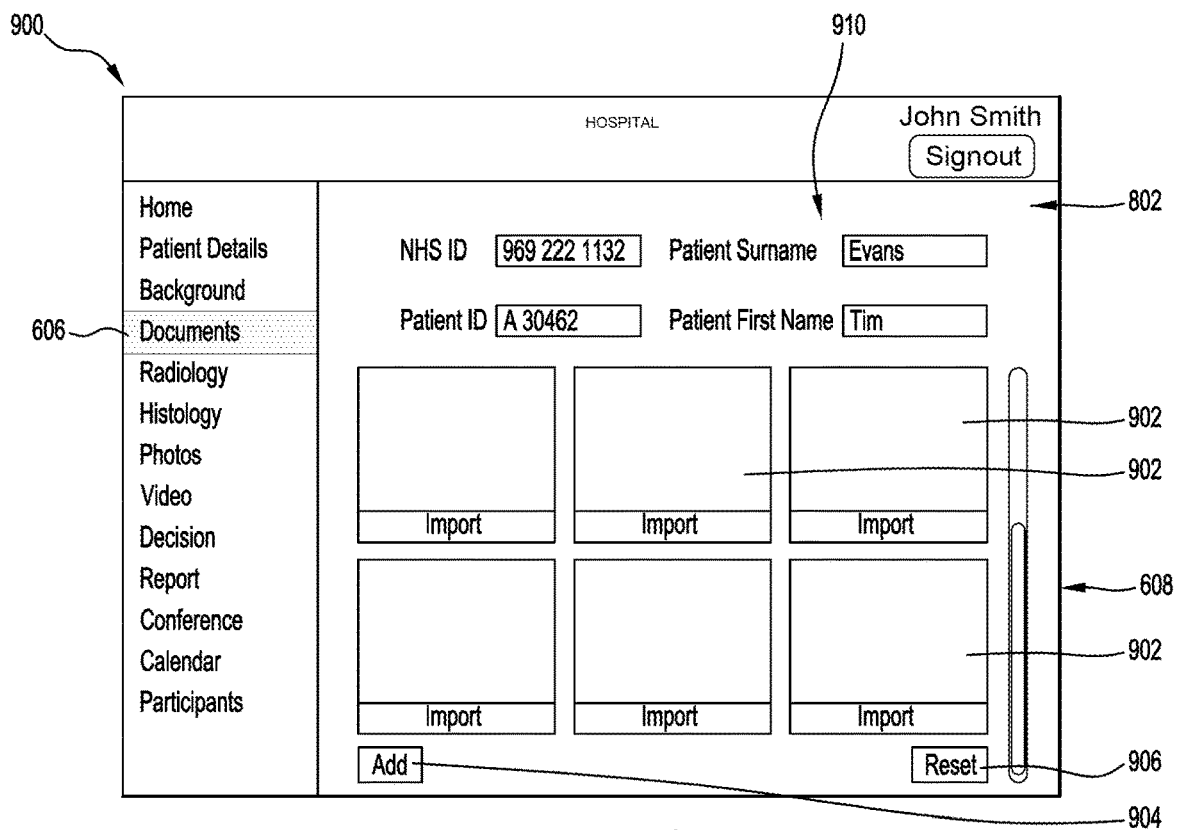

The web portal display 900 of FIG. 9 shows the information screen 910 associated with the documents topic option 606 displayed in the display window 608. Information screens associated with the radiology topic option 606, the histology topic option 606, the photos topic option 606, and the video topic option 606 may correspond with the information screen 910 of documents topic option 606.

As depicted, the information screen 910 shows the patient identification section 802 of FIG. 8 and a plurality of import panels 902. The information screen 910 also depicts a user selectable add option 904 and a user selectable delete option 906.

When the user identifies an import panel 902, for example by clicking on the import panel 902 and causing it to be highlighted, and selects the selectable add option 904, the user is provided with an option to select a document from a local or remote storage facility to associate with the data record stored at to the computer system 102 and/or the database 108. For example, in some embodiments, a document may be selected from memory 122 of the computing device 104, a USB or external memory coupled to the computing device 104, data memory 116 of the computer system 102 and/or the database 108. In some embodiments, selection of the add option 904 by a user causes the browser application 302 being executed by the processor 120 to send an association request to the data handling module 210 of the web portal application 202, at 422, as shown in FIG. 4. For example, the associate request may comprise data, such as the document, and/or an indication of a storage location of the data or a link to the location of the data. Referring to FIG. 5, in response to receiving the association request, the data module 210 associates the data with the data record, at 520 so that uploaded documents or links to the uploaded documents are stored in the data record of the case item 616. For example, the data handling module 210 may associate the data with the data record by storing the data from the association request in the data record, by storing the link indicated in the association request from the association request in the data record, and/or by retrieving data from the storage location indicated in the association request and storing it in the data record. In some embodiments, when a document has been selected and associated with the data record for the case, information pertaining to the document, such as the name of the file or a file cover image, is displayed in the identified import panel 902.

In some embodiments, selection of the delete option 906 triggers code of the browser application 302 to transmit a cancel or delete request to the data handling module 210 of the web portal application 202, at 418, as shown in FIG. 4. In response to receiving the cancel or delete request, the data handling module 210 is caused to delete the uploaded documents or links from data record, at 516, as shown in FIG. 5. In some embodiments, the data handling module 210 may cause the web server 220 to update page code associated with the web portal display 900 of the documents topic option 606. For example, when the user selectable delete option 906 is selected, a document associated with a highlighted import panel 902 which has been associated with the data record is removed or deleted, the information pertaining to the document is removed from the import panel 902.

In some embodiments, an index pane or search field (not shown) may be provided to allow keyword searching of a file, folder and/or database to identify a document which may then be dragged and dropped to a selected import panel 902.

The user may select the radiology topic option 606, the histology topic option 606, the photos topic option 606, and/or the video topic option 606 from the tab 602 to cause the automatic loading of the information screen 910 associated with the selected topic option 606 for display in the display window 608 and to allow the user to import, upload or associate data and/or links relating to radiology information, histology information, photos, and/or video clips, respectively, to the data record in a similar manner to that described above in connection with the documents topic option 606. In embodiments where the online meeting being conducted in the online collaboration environment is for an online meeting other than an MDT meeting, various topic options 606 may be associated with a similar information screen to information screen 910 displayed in the display window 608 to allow information to be imported, uploaded or associated with the data records of the case item 616.

Figure 10:
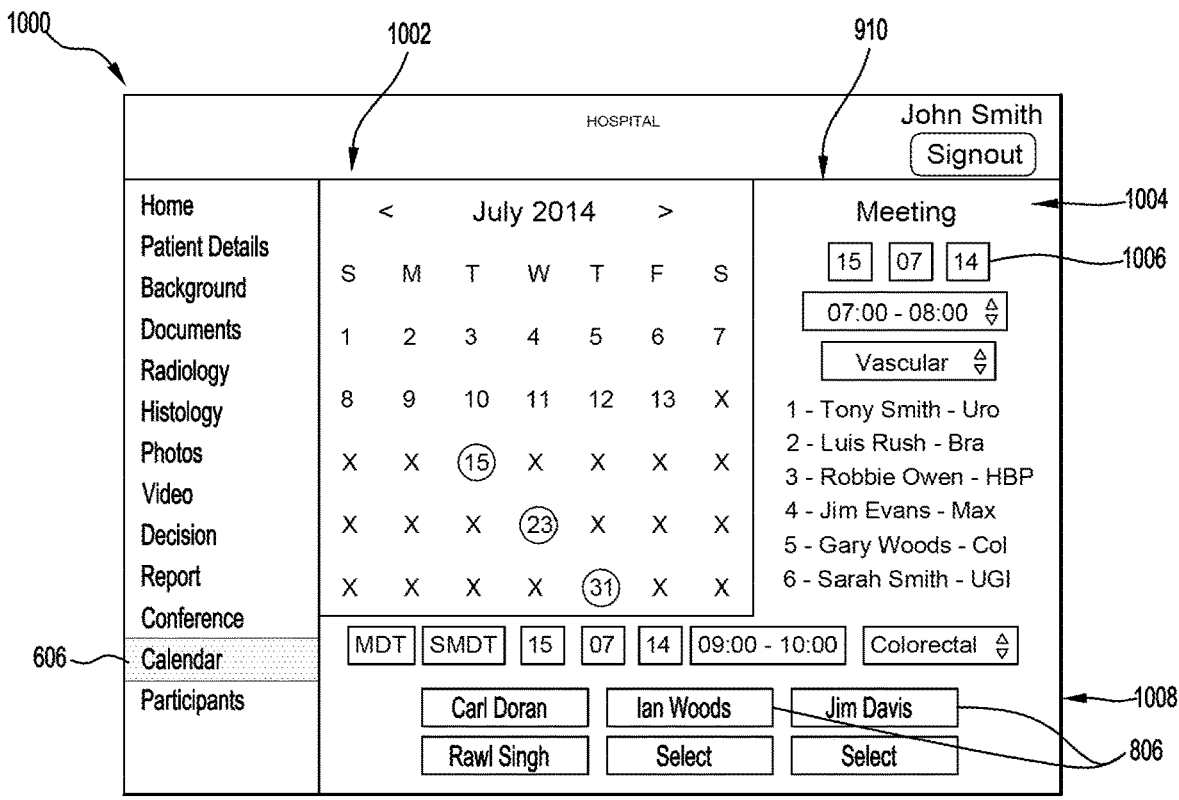

The user may select the calendar topic option 606 from the tab 602 to cause the automatic loading of an information screen 1010 associated with the calendar topic option 606 for display in the display window 608, as depicted in FIG. 10.

FIG. 1000 shows the information screen 1010 associated with the calendar topic option 606 for allowing a user, such as the collaborator, to review particulars of the online meeting being scheduled and other scheduled meetings. The information screen 1010 comprises a calendar portion 1002 wherein the selected date for the meeting is highlighted or otherwise visually identified and dates when other meetings have been scheduled are also highlighted or otherwise visually identified in a manner that distinguishes them from the selected date.

The information screen 1010 comprises pre-scheduled meeting details panel 1004 which displays information about pre-scheduled meetings for the selected date, including an identification of the invited or proposed participants. It is envisaged that multiple meetings relating to multiple subjects may occur during different time periods of the selected date. Accordingly, the pre-scheduled meeting details panel 1004 provides a user selectable drop-down time menu 1006 to allow a user select a different time and a user selectable drop-down subject menu to allow a user select a different subject. In response to the selection of a different time and/or subject, the meeting details panel 1004 displays information about the meeting scheduled for the selected time and/or subject on the selected date. For example, selection of a different time and/or subject may trigger code of the browser application 302 being executed by the processor 120 to request further page code from the web server 220, at 412, 414 of FIG. 4, and at 512 of FIG. 5, or to execute an applet within the code of the browser application 302 to display information associated with the selection.

The information screen 1010 comprises current meeting panel 1008 showing details of the meeting being scheduled including an participant identifier 1009 of an invited or proposed participants, the date, time and subject of the meeting and an indication of the type of meeting, such as an MDT or an SMDT. In some embodiments, the participant identifier 1009 may be user selectable and the browser application 302, in response to selection of the participant identifier 1009, may be caused to generate information screen 1300, as discussed below in relation to FIG. 13.

In some embodiments, the current meeting panel 1008 includes a user selectable submit or invite option (not shown) to cause an invitation request to be transmitted to the party(s) identified by the participant identifier 1009. For example, selection by the user of the user selectable submit or invite option (not shown), may trigger code of the browser application 302 being executed by the processor 120 to cause the computing device 102 to transmit an invitation request to the party(s) identified by the participant identifier 1009 at 424, as shown in FIG. 4. Alternatively, selection by the user of the user selectable submit or invite option (not shown), may trigger code of the browser application 302 being executed by the processor 120 to cause an invitation notification, including an identification of at least one party, to be transmitted to the notification module 212 of the web portal application 202, at 424, as shown in FIG. 4. Referring to FIG. 5, in response to receiving the invitation notification, the notification module 212 may be caused to issue or transmit invitation request(s) to the identified party(s), at 522. For example, the invitation request may be an email and/or a calendar invite. In some embodiments, the invitation request may include a read receipt.

In some embodiments, the current meeting panel 1008 includes a user selectable confirmation option (not shown) to cause a confirmation notification to schedule the meeting to be transmitted by the browser application 302 to the data handling module 210 of the web portal application 202, at 426, as shown in FIG. 4. Referring to FIG. 5, in response to receiving the confirmation notification from the browser application 302, the data handling module 210 may cause the computer system 202 to notify the VCS 110 of the scheduled meeting, at 524. For example, the processor 112 may execute code to cause the data handling module 210 to transmit a scheduled meeting notification to the VCS 110 or may cause the session management module 218 of the collaboration application 204 to transmit a scheduled meeting notification to the VCS 110. For example, the scheduled meeting notification may include a scheduled time for the meeting and an identifier of the computing devices 104 associated with the participants invited to the meeting. In some embodiments, the scheduled meeting notification may include a meeting session identifier. In other embodiments, the VCS 100 may generate a meeting session identifier for the schedule meeting and associate the identifier(s) of the computing devices 104 associated with the participants invited to the meeting with the meeting session identifier.

Figure 11:
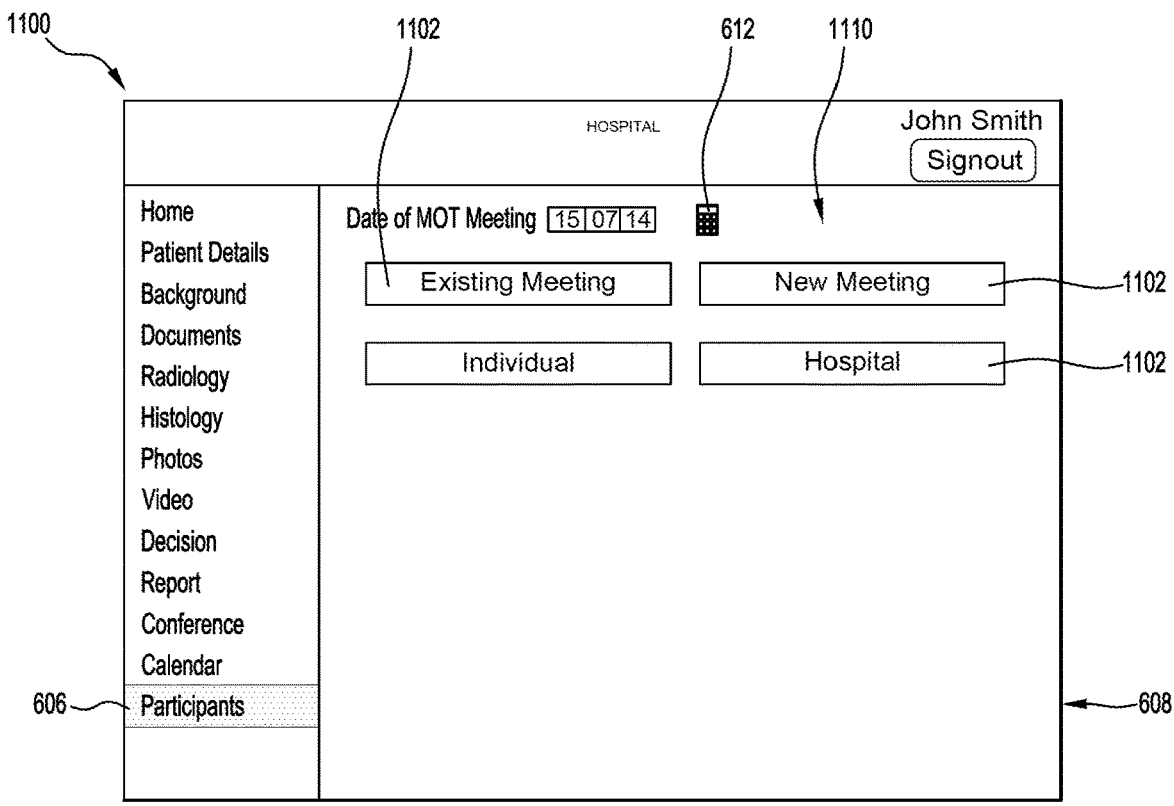

The user may select the participants topic option 606 from the tab 602 to cause the automatic loading of an information screen 1110 associated with the participants topic option 606 for display in the display window 608, as depicted in FIG. 11. As shown, the information screen 1100 depicts the user selectable calendar option 612 of FIG. 6 and an indication of the currently selected date and a plurality of user selectable participant type options 1102, including an individual and a hospital for the present case of a multidisciplinary meeting.

In response to selection by the user of a user selectable participant type options 1102 for an individual, an associated information screen 1210 is automatically displayed in the display window 608, as depicted in FIG. 12. In response to selection by the user of a user selectable participant type options 1102 for an hospital, an associated information screen 1310 is automatically displayed in the display window 608, as depicted in FIG. 13. The information screen 1200, 1300 provides a participant form 1202, 1302 for population with details pertaining to the participant such as the individual's name, specialty, associated hospital, the individual's contact details, the hospital name and contact details. In some embodiments, the information screen 1200, 1300 provides a user selectable option (not shown) to cause the participant identifier 1009 to be depicted in the current meeting panel 1008 of the information screen 1010 as depicted in FIG. 10.

In some embodiments, the information screen 1200, 1300 provides a user selectable submit or invite option (not shown) to cause an invitation request to be transmitted to the party identified in the participant form 1202, 1302. For example, selection by the user of the user selectable submit or invite option (not shown), may trigger code of the browser application 302 being executed by the processor 120 to cause the computing device 102 to transmit an invitation request to the party identified in the participant form 1202, 1302 at 424, as shown in FIG. 4. Alternatively, selection by the user of the user selectable submit or invite option (not shown), may trigger code of the browser application 302 being executed by the processor 120 to cause an invitation notification, including an identification of at least one party, to be transmitted to the notification module 212 of the web portal application 202, at 424, as shown in FIG. 4. Referring to FIG. 5, in response to receiving the invitation notification, the notification module 212 may be caused to issue or transmit an invitation request to the identified party, at 522. For example, the invitation request may be an email and/or a calendar invite. In some embodiments, the invitation request may include a read receipt.

Once a meeting has been scheduled, an authorised user, such as a consultant associated with the case item 616, may be provided with relevant credentials to allow them to login to the web portal to review the case information in advance of the scheduled online meeting.

Figure 14:
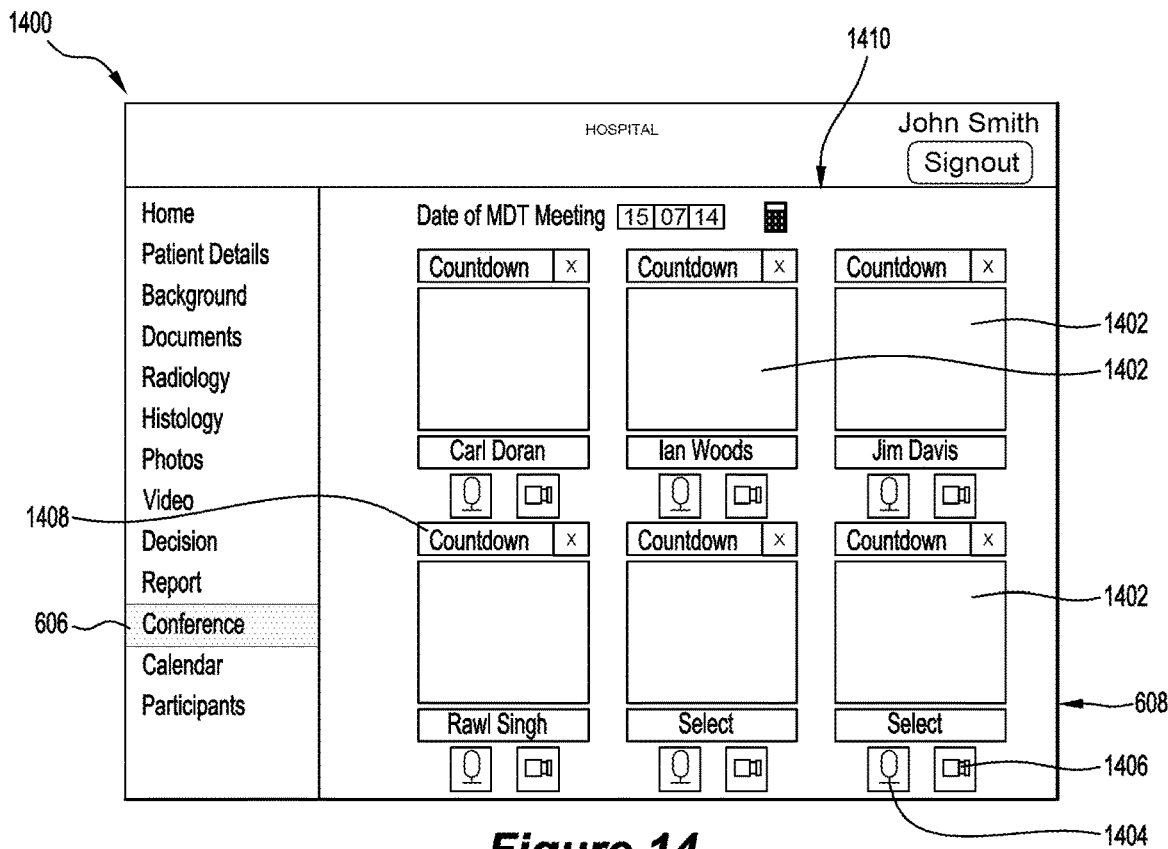
Figure 15:
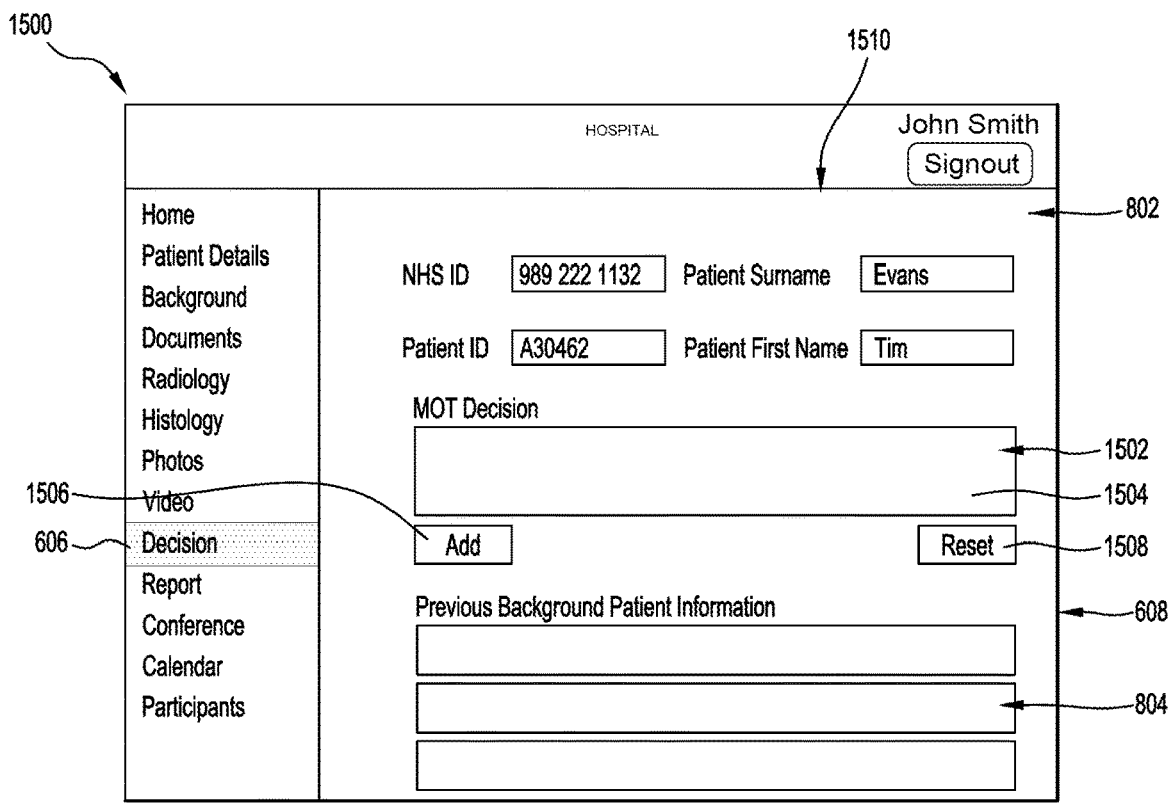
Figure 16:
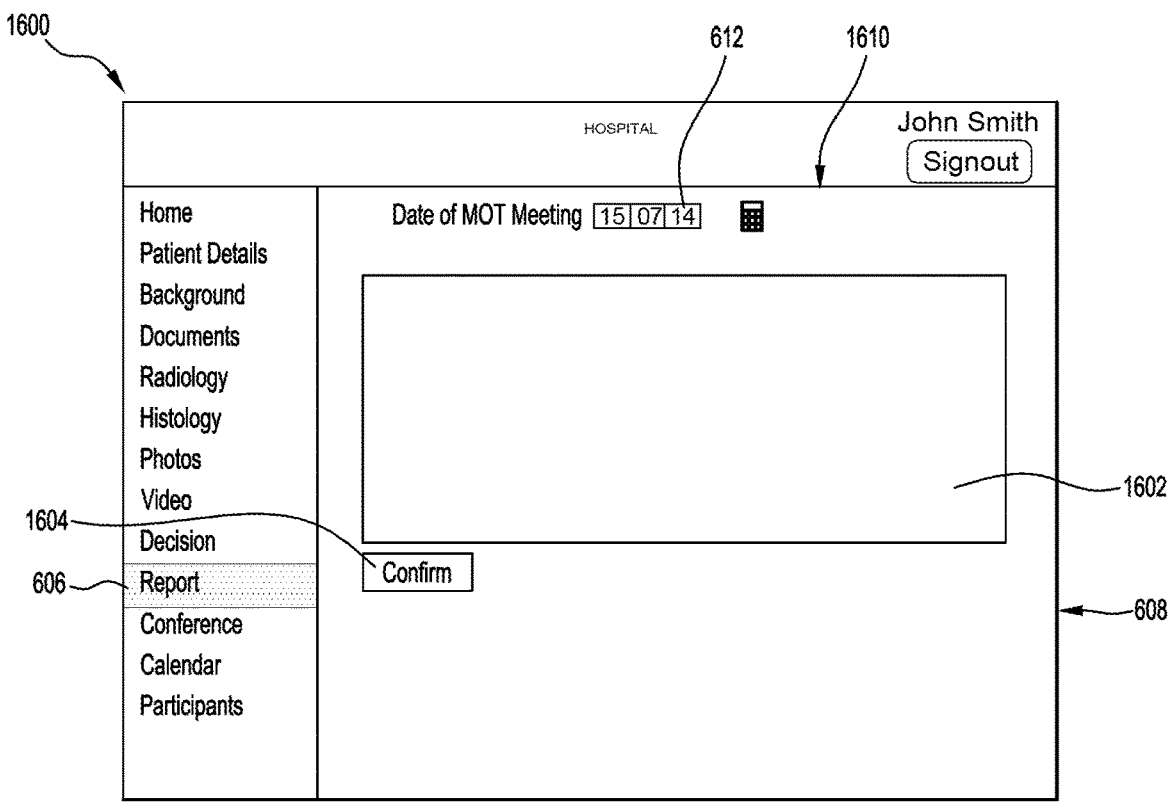

FIGS. 14, 15 and 16, show exemplary web portal displays 1400, 1500, 1600, of a webpage or a web portal viewable on the user interface 124 of the computing device 104, according to some embodiments. The web portal displays 1400, 1500, 1600, are generated by the browser application 302 in response to code served by the computer system 102 in accordance with the web portal application 202.

In some embodiments, the web portal displays 1400, 1500, 1600, may be employed by a user or coordinator of an online meeting during a scheduled meeting and/or following a conclusion of a scheduled meeting, as is described below in connection with FIGS. 17, 18, 19, 20 and 21.

A user may select the decision topic option 606 from the tab 602 to cause the automatic loading of an information screen 1410 associated with the conference topic option 606 for display in the display window 608, as depicted in FIG. 14.

The information screen 1410 associated with the conference topic option 606 depicts the user selectable calendar option 612 of FIG. 6 and an indication of the currently selected date. The information screen 1410 also shows a plurality of conference screens 1402, each conference screen 1402 arranged to be associated a user invited to participate in a meeting scheduled for the depicted date/time. In particular, the conference screen 1402 is configured to be associated with a user interface 124, such as a camera, of a computing device 104 to display a live video feed from the camera of the computing device 104 during a scheduled online meeting.

For example, each conference screen 1402 may be associated with a media stream received from a computing device 104 associated with a user participating in the online meeting and relayed by the VCS 110 to the computing device 104 displaying the web portal on the user interface 124. In some embodiments, the stream control module 308 of the stream control application 306 of the collaboration application 204 cooperates with the browser application 302 to feed or convey the streams associated with a meeting session identifier for the schedule meeting received from the VCS 110 to the user interface 126 of the computing device 104 for display in the conference screens 1402. In some embodiments, a conference screen 1402 of the plurality of conference screens 1402 may be associated with or coupled to a local video/audio feed received from the user interface 124 of the computing device 104.

Each conference screens 1402 is associated with a user selectable speaker on/off icon 1404 and a user selectable video on/off icon 1406 to allow the user to selectively control one or more of the users or participants participation in the online meeting. The video on/off icon 1404 is provided to allow the user of the web portal to control a video feed of the computing device 104 associated with conference screens 1402, for example, to control whether or not the user or participant associated with the conference screen 1402 is visible to other users of the online collaboration environment, i.e. to blank their video feed. The audio on/off option 1406 is provided to allow the user of the web portal to control an audio feed of the computing device 104 associated with conference screens 1402, for example, to control whether or not the user or participant associated with the conference screen 1402 is audible to other users of the online collaboration environment, i.e., to mute their audio.

In some embodiments, selection of the video on/off option 1404 and/or audio on/off option 1406 triggers code of the browser application 302 being executed by the processor 120 to transmit a request to the data handling module 210 of the web portal application 202 which in turns sends the audio/video control request directly to the VCS 110 or to the session management module 218 of the collaboration application 204, at 428, as shown in FIG. 4. For example, the request may include an identifier of the computing device 204 and/or the stream identifier associated with the video/audio feed to be controlled. As depicted in FIG. 5, in response to receiving the request from the data handling module 210 of the web portal application 202, the session management module 218 may issue a command, which may include an identifier of the computing device 204 and/or the stream identifier associated with the video/audio feed to be controlled and/or the meeting session identifier, to the VSC 110 to cause the VSC 110 to turn on/off the audio/video of the stream associated with computing device 104 or the stream identifier being broadcast to the other computing devices 104 associated with the meeting session identifier, at 526. In some embodiments, in response to receiving the audio/video control request from the browser application 302, the data handling module 210 of the web portal application 202 causes the web server 220 of the collaboration application 204 (directly or via data handling module 216) to transmit code to the browser application 302 of the computing devices 104 associated with the speaker only or to the browser application 302 of some or all of the computing devices 104 for execution by processor 120 to cause the collaboration display to depict a stopwatch (not shown), as discussed below with reference to FIG. 19.

In some embodiments, each conference screens 1402 is associated with a user selectable countdown option 1408 to allow the user to send a warning to a participant who is speaking to indicate that they have a limited amount of time remaining before their audio/video will be muted/blanked, for example, to cue the speaker associated with the conference screen 1402 that he/she is overrunning and is due to be asked to hand over the discussion to another delegate. In some embodiments, selection of the user selectable countdown option 1408 triggers code of the browser application 302 being executed by the processor 120 to transmit a request for code to the data handling module 210 of the web portal application, at 412, as shown in FIG. 4. Referring to FIG. 5, at 512, in response to receiving the countdown request, the data handling module 210 of the web portal application 202 causes the web server 220 of the collaboration application 204 (directly or via data handling module 216) to transmit code to the browser application 302 of the computing devices 104 associated with the speaker only or to the browser application 302 of some or all of the computing devices 104 for execution by processor 120 to cause the collaboration display to depict a flashing conference screen 1920 and/or a stopwatch (not shown), as discussed below with reference to FIG. 19.

The user may select the decision topic option 606 from the tab 602 to cause the automatic loading of an information screen 1510 associated with the decision topic option 606 for display in the display window 608, as depicted in FIG. 15.

As depicted, the information screen 1510 shows the patient identification section 802 of FIG. 8 and the previous background patient information field 808 for receiving previous background information relating to the patient, also depicted in FIG. 8. The information screen 1510 also show a MDT decision form 1502 comprising a decision information field 1504, such as a text box, for receiving decision information to the case and/or patient. The decision information field 1504 is arranged to receive text inputted by the user via the user interface 124 of the computing device 102.

The MDT decision form 1502 also depicts a user selectable add option 1506 to allow the decision information inserted into the information field 1504 to be saved in connection with the case item 516. In some embodiments, selection of the add option 1506 triggers code of the browser application 302 being executed by the processor 120 to transmit the inputted decision information to the data handling module 210 of the web portal application 202, at 418, as shown in FIG. 4. In response to receiving the decision information, the data handling module 210 may store the information in the data record associated with the case item 616, at 516, as shown in FIG. 5. In some embodiments, the data handling module 210 may pass the decision information and/or a link to the decision information, to the collaboration application 204, as discussed below with reference to FIGS. 17 to 23.

In some embodiments, the user may select the report topic option 606 from the tab 602 to cause the automatic loading of the information screen 1610 associated with the report topic option 606 for display in the display window 608, or indeed the user may select any topic option 606 from the tab 602 to cause the automatic loading of an information screen associated with the selected topic option 606 for display in the display window 608. Selection of a topic option 606 by the user may trigger code of the browser application 302 being executed by the processor 120 to request and receive further page code from the web server 220, at 412, 414, of FIG. 4 and 512 of FIG. 5, or to execute an applet within the code of the browser application 302 to display information associated with the selected topic option 606. In some embodiments, selection of the user selectable add option 1506 may cause automatic highlighting or otherwise visual identification of the report topic option 606 and the automatic display of an information screen 1610 associated with the report topic option 606 in the display window 608.

The MDT decision form 1502 also depicts a user selectable reset option 1508 to cancel or delete the information inserted into the decision information field 1504 and/or to revert to a previously selected topic option 606 or the home topic option 606 and the associated information screen. In some embodiments, selection of the reset option 1508 triggers code of the browser application 302 to transmit a cancel or delete request to the data handling module 210 of the web portal application 202, at 416 of FIG. 4 and in response to receiving the cancel or delete request, the data handling module 210 may delete decision information from the data record and may cause the web server 220 to update page code associated with web portal display 1500 of the decision topic option 606.

As depicted, the information screen 1610 associated with the report topic option 606 shows the user selectable calendar option 612 of FIG. 6 and indicates a currently selected date. Report information associated with the selected date is presented in a report information field 1602 of the information screen 1600. For example, the report information may include information detailing a proposed and agreed course of action for managing or handling an item or situation. For example, in the event that the online meeting is an online multidisciplinary meeting, the report information may include information outlining findings and recommendations discussed at the online meeting. In some embodiments, the data handling module 210 may comprise code, which when executed by the processor 112, causes the generation of the report information based on information received by the data handling module 216 of the collaboration application 204 during the online meeting and passed the data handling module 210 of the web portal application 202.

The user selectable calendar option 612 allows a user to select a different date which is then indicated on the information screen 1610 and which causes the presentation of report information associated with the selected date to be presented in a report information field 1602. In some embodiments, selection of a calendar date using the calendar option 618 triggers code of the browser application 302 being executed by the processor 120 to request and receive further page code from the web server 220 at 412, 414, of FIG. 4 and 512 of FIG. 5, or to execute an applet within the code of the browser application 302 to display report information associated with the selected date.

The information screen 1610 also depicts a user selectable confirm option 1604 to allow the user to confirm or approve the report information presented in the report information field 1602 of the information screen 1610. In some embodiments, selection of the confirm option 1604 triggers code of the browser application 302 being executed by the processor 120 to transmit an approval request to the data handling module 210 of the web portal application 202, at 418, as shown in FIG. 4, to cause the data handling module 210 to record the user's approval of the report information in the data record associated with the case item 616, at 516, as shown in FIG. 5.

Figure 17A:
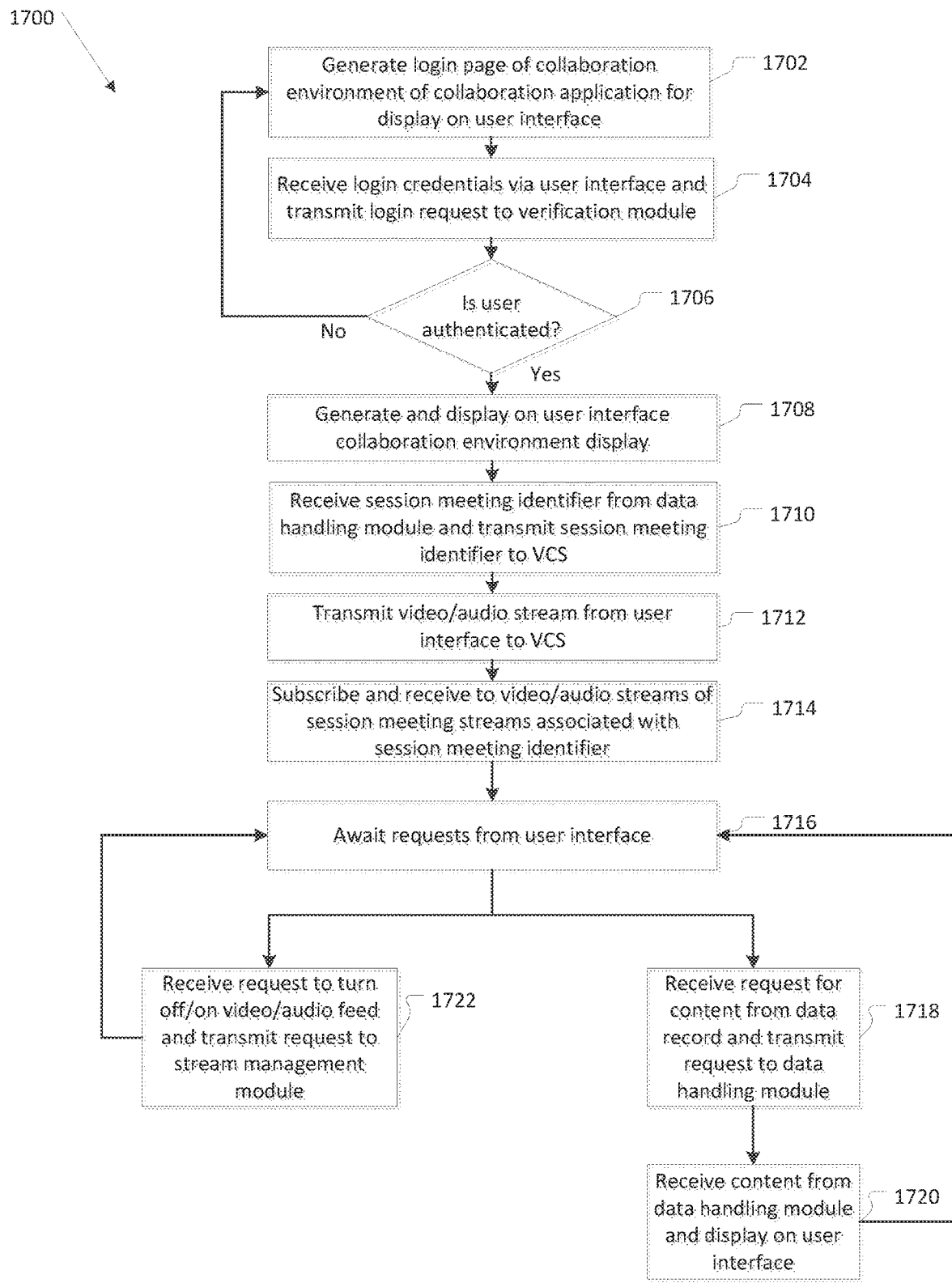
FIGS. 17A and 17B show a process flow diagram depicting a method of conducting or controlling an online meeting in an online collaboration environment facilitated by a collaboration application hosted on the computer system of FIG. 1, the method implementable by at least one of the computing devices of FIG. 1, according to some embodiments.
Figure 17B:
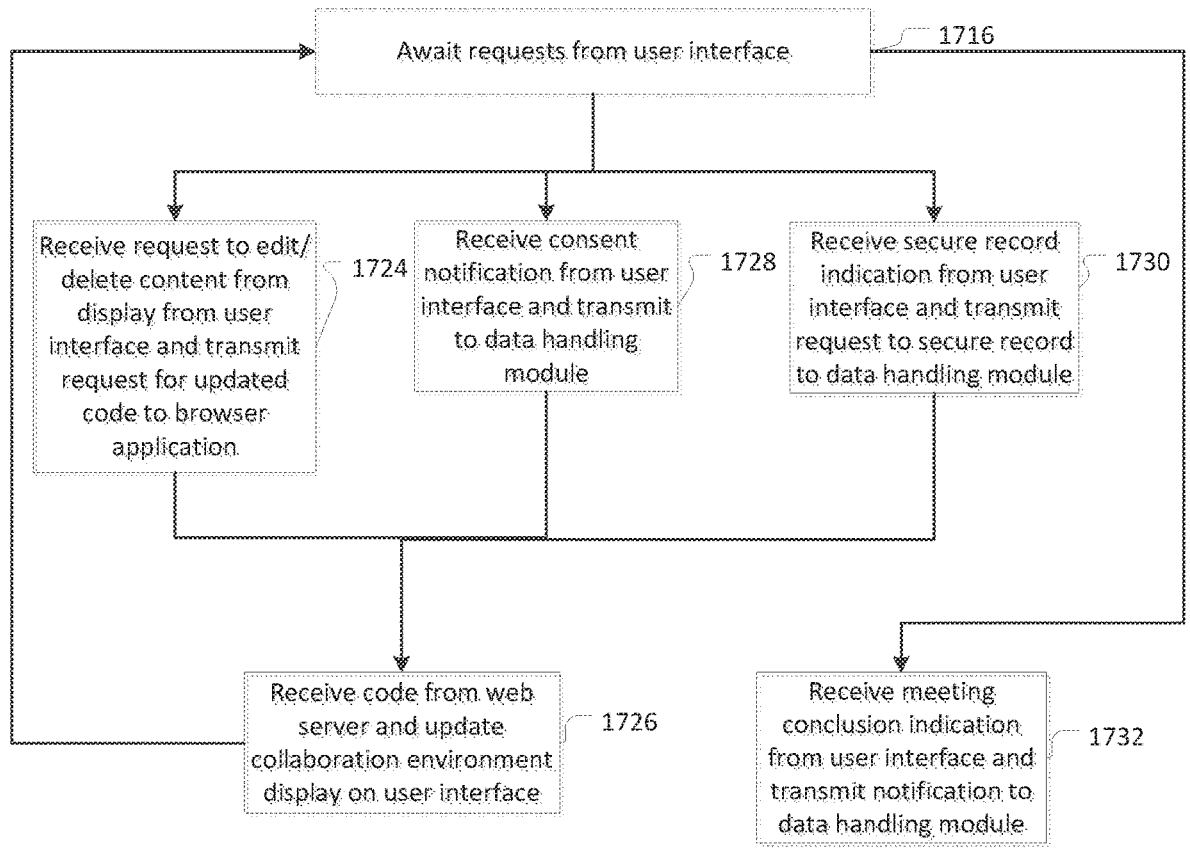

FIG. 17 is a process flow diagram of a method 1700 of coordinating or controlling an online meeting, operable on one of the computing device 104 of the communications system 100, according to some embodiments. In particular, the method 1700 is facilitated by the computer system 102 based on code served by the computer system 102 to one or more of the computing devices 104. Therefore, the acts described in relation to the method 1700 are performed by execution in browser application 302 of browser-executable code served to the computing device 104 by the computer system 102.

Figure 18:
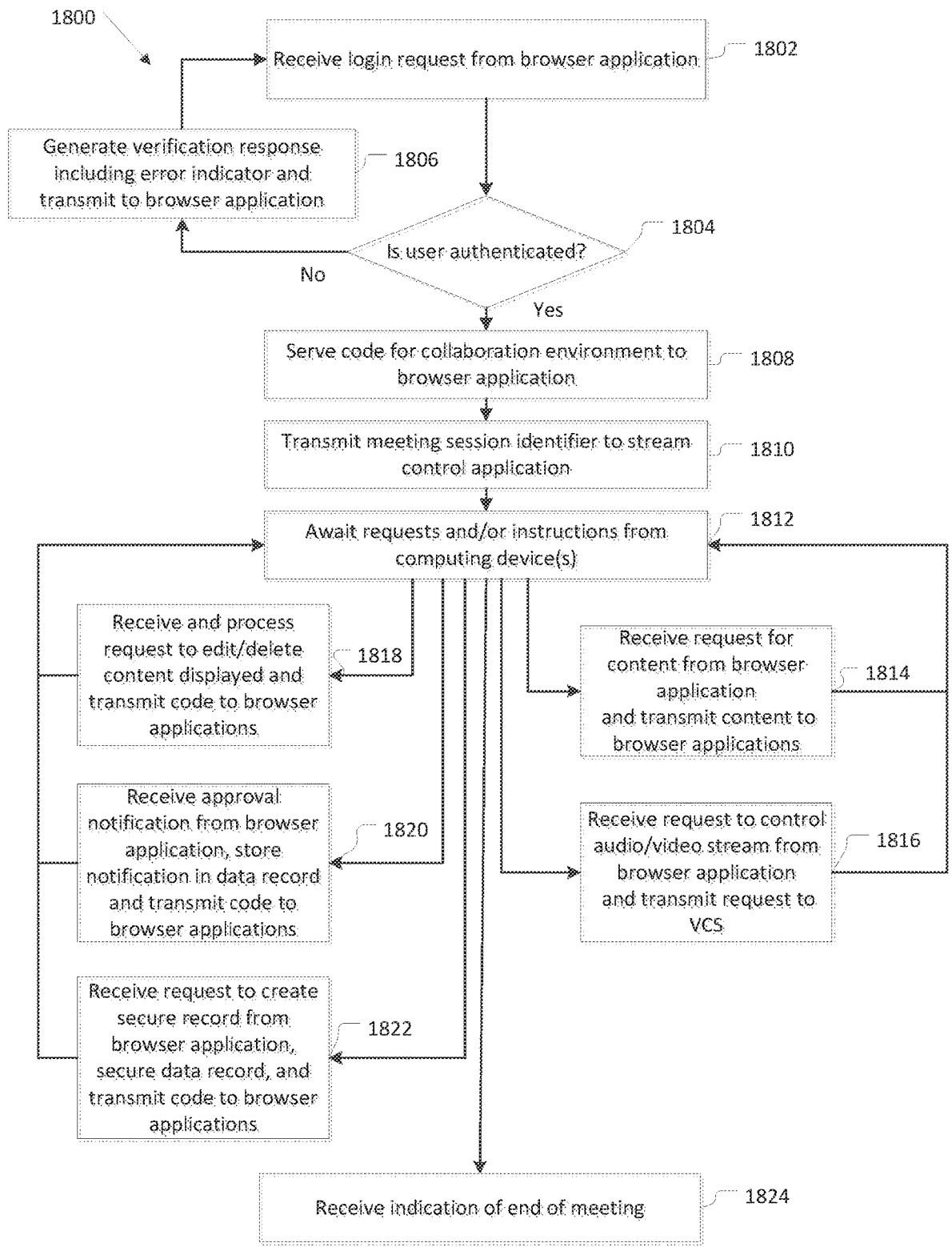
FIG. 18 is a process flow diagram depicting a method of conducting or controlling an online meeting in an online collaboration environment facilitated by a collaboration application hosted on the computer system of FIG. 1, the method implementable by the computer system of FIG. 1, according to some embodiments.

FIG. 18 is a process flow diagram of a method 1800 of coordinating or controlling an online meeting, operable on the computer system 102 of the communications system 100, according to some embodiments.

The methods 1700, 1800 are described with reference to FIGS. 19 to 23, which show exemplary collaboration environment displays 1900, 2000, 2100, 2200, 2300 of a collaboration environment viewable on the user interface 124 of the computing device 104, according to some embodiments. The collaboration environment displays 1900, 2000, 2100, 2200, 2300 are generated by the browser application 302 in response to code served by the computer system 102 in accordance with the online collaboration application 204.

Referring to FIG. 17, the method 1700 begins with the browser application 302 generating a login page (not shown) of a collaboration environment of the online collaboration application 204 for display on the user interface 124 in response to code served by the computer system 102 in accordance with the collaboration application 204, at 1702. In some embodiments, a user such as a participant or coordinator, is provided with sign-in details or credentials, for example, a username and password, which may be employed to securely access the collaboration application 204 for participating in and/or coordinating online meetings. Forgotten or misplaced usernames and passwords may be recovered for a user using details provided during a signup process.

In some embodiments, the browser application 302 receives login credentials via the login page of the collaboration environment which triggers the processor 120 of the computing device 104 to execute code of the browser application 302 to cause a login request to be transmitted to the computer system 102 for verification, at 1704.

In some embodiments, the credentials associated with the user may be employed to determine the collaboration environment to be displayed to the user. For example, the credentials may be associated with at least one access request which may dictate which of a plurality of collaboration environment displays and/or content is to be displayed to the user on the user interface 124 of the computing device 104. For example, a username may be associated with multiple passwords, where each combination of username and password corresponds to a particular access request for a collaboration environment. In some embodiments, a user may have login credentials for meetings in which they are authorised users having permissions to perform authorised user functions, such as a collaborator, and the user may also have login credentials for meetings in which they are participants and do not have permissions to perform authorised user functions.

Referring to FIG. 18, the computer system 102 receives the login request, at 1802, which triggers the processor 112 of the computer system 102 to execute the verification module 214 of the collaboration application 204 to cause the computer system 102 to determine whether or not the credentials are valid and whether the user is authorised to access the collaboration application 204, at 1804. For example, the computer system 102 may be configured to compare the credentials submitted by the user with authorised coordinator details stored locally in data memory 116 or at database 108.

If the verification module 214 deems that the user is unauthorised, the verification module 214 may cause a verification response including an error indicator to be transmitted to the browser application 302, at 1806.

Referring to FIG. 17, when the computing device 104 receives the verification response including the error indicator, the browser application 302 is caused to regenerate the login page (not shown) of the collaboration environment for display on the user interface 124, at 1702. In some embodiments, the browser application 302 may generate and display an error message on the user interface 124 of the computing device 104.

Referring to FIG. 18, if the verification module 214 deems the user authorised, the web server 220 causes the computer system 102 to serve code, such as HTML text for the collaboration environment, to the browser application 302 of the computing device 104 to cause the browser application 302 to show a collaboration environment display 1900, 2000, 2100, 2200, 2300 on the user interface 124, at 1808. In some embodiments, the verification module 214 may also cause a verification response including an authorisation indicator to be transmitted to the browser application 302.

Referring again to FIG. 17, receipt of code, such as HTML text for the collaboration environment, from the web server 220 causes the browser application 302 to show a collaboration environment display 1900, 2000, 2100, 2200, 2300 on the user interface 124, at 1708, to allow user to participate in and/or control or coordinate online meetings in the online collaboration environment.

Referring to FIG. 18, if the verification module 214 deems the user authorised, the session management module 218 of the collaboration application 204 may provide a meeting session identifier assigned to the scheduled meeting to the stream control application 306 of the computing device 104, at 1810 to enable the computing device to cooperate with the VCS 110. The collaboration application 204 may then await requests and/or instructions from the computing device(s) 104, at 1812.

Referring again to FIG. 17, in response to receiving the meeting session identifier from the session management module 218 of the collaboration application 204, the stream control module 208 of the stream control application 306 may be caused to transmit the meeting session identifier to the VCS 110, at 1710. In this way, the VCS 110 can associate streams received from the computing device 104 with an intended or correct online meeting.

The computer system 102 may also to serve code to the stream control application 306 to cause the stream publisher module 310 of the stream control application 306 to transmit or publish a local video/audio stream from the user interface 124 of the computing device 104 to the VCS 110, at 1712. The computer system 102 may also to serve code to the stream control application 306 to cause the stream subscriber module 312 of the stream control application 306 to send a request to the VCS 110 to subscribe to the video/audio streams associated with the meeting session identifier to thereby receive the streams associated with the meeting, at 1714. For example, in some embodiments, receipt of the meeting session identifier from the session management module 218 of the collaboration application 204, causes the stream publisher module 310 to publish a local video/audio stream from the user interface 124 and causes the stream subscriber module 312 to subscribe to the video/audio streams associated with the meeting session identifier. In this way, the VCS 110 is capable of relaying audio/video streams received by the VCS 110 from other user interfaces 124 of the computing devices 104 to the stream control module 308 of stream control application 306. The stream control application 306 cooperates with the browser application 302 to output the audio/video streams to the user interface 124. The browser application 302 may then await requests and/or instructions from the user interface 124, at 1716.

Figure 19:
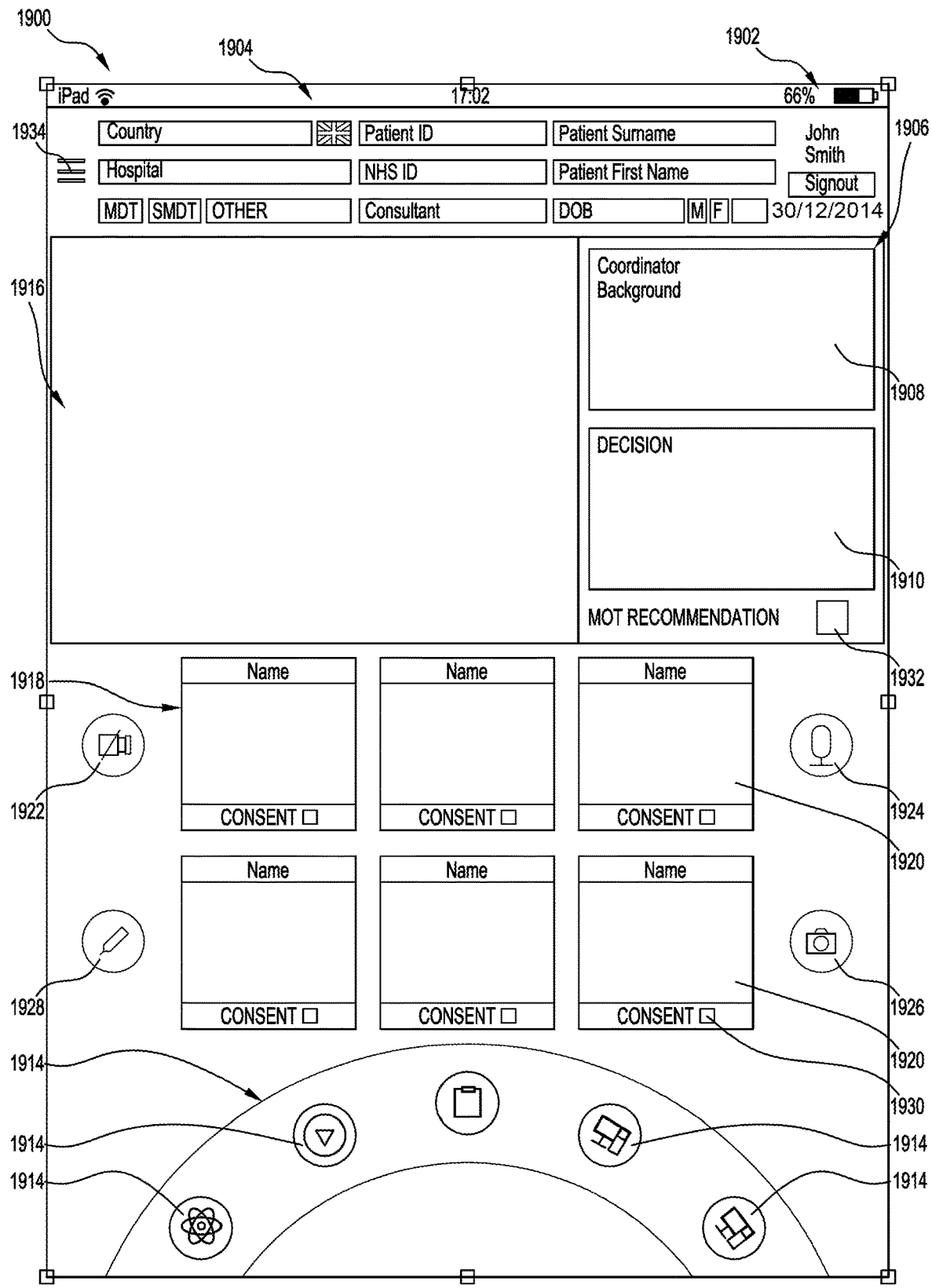
FIGS. 19 to 23 show example displays of an online collaboration environment shown on a user interface of one of the computing device of FIG. 1, according to some embodiments.

Referring to FIG. 19, there is shown an online collaboration environment display 1900, for example, as may be generated by the browser application 302 in response to code received from web server 220 at 1708, and presented to an authorised user, such as a participant, on user interface 124. Collaboration environment display 1900 shows a user-specific information section 1902, which displays user details, for example, the user's name, a sign-out selectable option to allow the user to sign-out or securely exit the online collaboration environment, and the current date.

The collaboration environment display 1900 includes a patient information section 1904, providing details pertaining to a patient for which an online team meeting is being conducted. For example, the patient information section 1904 may include information such as the patient's surname and first name, their date of birth, an identification number, such as a hospital patient ID or NHS ID, the hospital which is associated with or responsible for the patient's treatment, the country in which the hospital and/or patient is based, an identification of the consultant responsible for the patient, the patient's condition, for example, a type of cancer, and/or an indication of whether the collaboration meeting is a multidisciplinary team meeting (MDT) or a specialist multidisciplinary team meeting (SMDT). In embodiments where the online meeting being conducted in the online collaboration environment is for an online meeting other than an MDT or SMDT, the collaboration environment display 1900 may include an information section to provide details pertinent to the type of meeting being conducted.

The collaboration environment display 1900 shows a case detail panel 1906 displaying an identification of a coordinator for the online meeting and including a background section 1908 detailing information pertinent to the patient and the patient's condition.

In some embodiments, the information displayed in the patient information section 1904 and the case detail panel 1906 is retrieved from the data record associated with the case item 616. For example, the data record may comprise information received from a user, such as a coordinator of the online meeting via the web portal application 202 in advance of the online meeting, as discussed above with reference to FIGS. 4 to 16. For example, the data handling module 216 of the collaboration application 204 deployed on the computer system 102 may retrieve the information from the data record, which may be stored in data memory 116 and/or database 108 and may serve code to the browser application 302 in accordance with the collaboration application 204 to cause the browser application 302 to display the information on the user interface 126 of the computing device 104.

Figure 21:
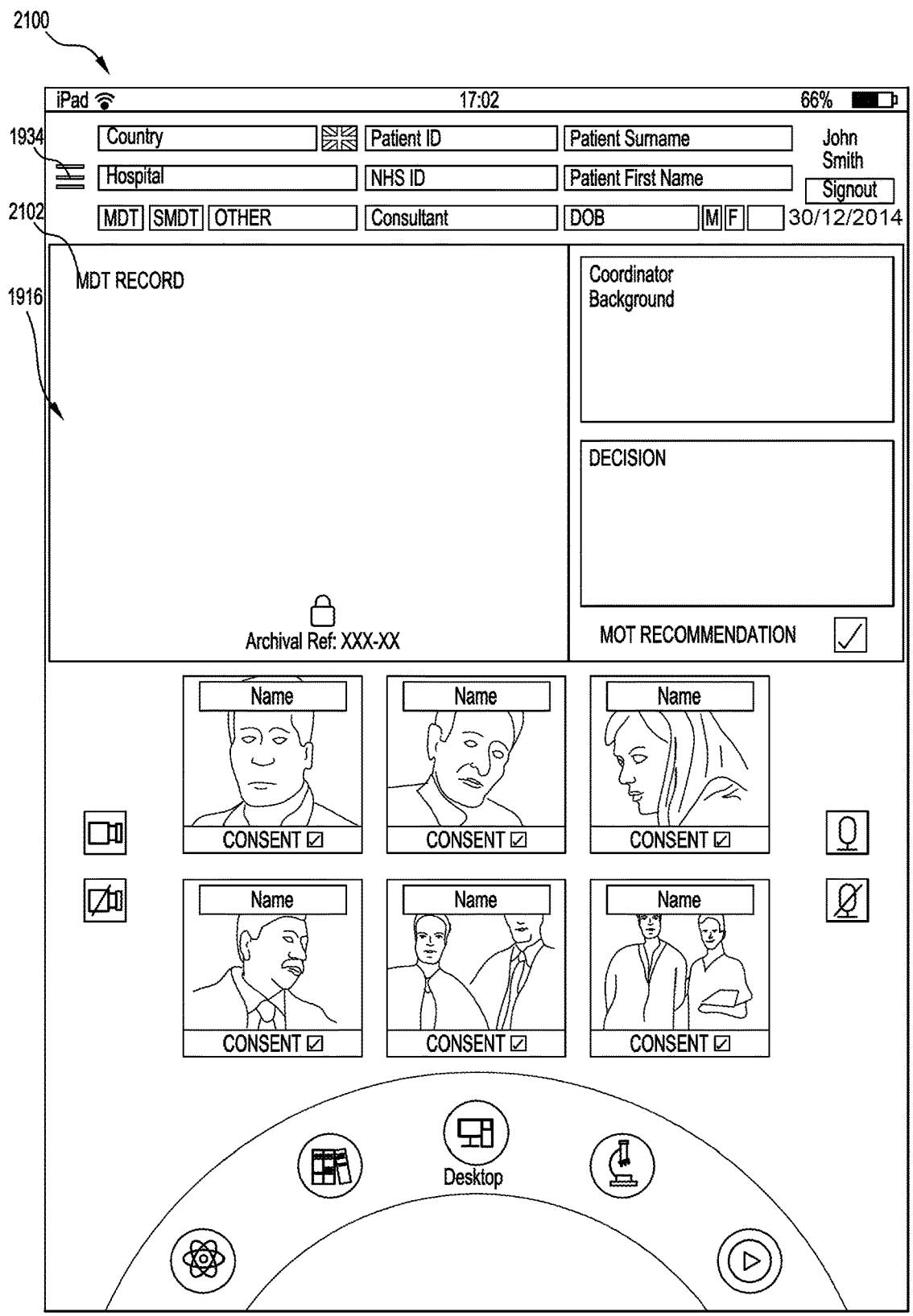

The collaboration environment display 1900 shows a decision panel 1910. The decision panel 1910 is a text box and is configured to display text inputted via a user interface 124 of a computing device 102. For example, once a patient's case has been discussed and a decision as to how the case and/or patient is to be handled is reached, the decision can be inputted via a user interface 124 of a computing device 102 and displayed in the decision panel 1910 as shown in FIG. 21. In some embodiments, only authorised users, such as the coordinator, are associated with permissions to enter, edit and/or delete text in the decision panel 1910. For example, in some embodiments, the user or coordinator may enter, edit and/or delete text in the decision panel 1910 using the web portal application 202 as discussed above with reference to FIGS. 4 to 16.

The collaboration environment display 1900 shows a file structure 1912, depicted as a navigation wheel, comprising a plurality of user selectable icons 1914 representing file folders of the file structure 1912, each file folder being associated with an information category. Each icon 1914 may be associated with an information category. In some embodiments, each icon 1914 may be associated with a file or data of the data record stored in the data memory 116 or the database 108. For example, as depicted, the icons 1914 of the exemplary collaboration environment display 1900 may comprise Checklist, Desktop 1, Desktop 2, Documentation, Histopathology, Metrics, Photos, Radiology, and Video, where each icons 1914 provides access to a data storage comprising documents and/or files associated with the icon 1914.

The collaboration environment display 1900 shows a discussion pane or a content display panel 1916 for displaying content relevant to the patient or case. A user may interact with the collaboration environment display 1900 via the user interface 124 of the computing device 104 to select the user selectable icons 1914 to select content from the associated folders of the file structure 1912 for display in the content display panel 1916, as shown in the collaboration environment display 2000 of FIG. 20. In some embodiments, only an authorised user, such as the coordinator, may select content for display in the content display panel 1916. For example, the content display panel 1916 may be used to focus discussion on the content depicted therein and/or to support or provide reference for a discussion point.

In some embodiments, selection of an icon 1914 triggers code of the browser application 302 being executed by the processor 120 to request content associated with the icon 1914 from the data handling module 216 of the collaboration environment application 204, at 1718, as shown in FIG. 17. In response to receiving the request for content from the browser application 302, the data handling module 216 retrieves the relevant content from the data record and transmits the content or a link to the content to the browser applications 302 of the computing devices participating in the online meeting, at 1814, as shown in FIG. 18. Referring again to FIG. 17, the browser application 302 receives the content or link to the content from the data handling module 216 and displays the content in the content display panel 1916, at 1720.

Referring again to FIG. 19, the collaboration environment display 1900 shows a conference pane or window 1918 comprising a plurality of conference panels or screens 1920. The conference window 1918 may depict live feeds from a plurality of computing devices 104 to thereby allow a number of users associated with computing devices 104 at remote locations to participate in an online meeting. For example, each conference screen 1402 may be associated with a media stream having a stream identifier received from a computing device 104 associated with a user participating in the online meeting and relayed by the VCS 110 to the computing devices 104 displaying the collaboration environment.

In some embodiments, the stream control module 308 of the stream control application 306 cooperates with the browser application 302 to feed or convey the streams associated with the session identifier received from the VCS 110 to the user interface 126 of the computing device 104 for display in the conference screens 1920. For example, each conference screen 1920 may be associated with a media stream having a stream identifier received from a computing device 104 associated with a user participating in the online meeting and relayed by the VCS 110 to the computing devices 104 displaying the collaboration environment. In some embodiments, the VSC 110 does not relay the stream received from the stream control application 306 back to the same stream control application 306 but instead, a conference screen 1920 of the plurality of conference screens may be associated with or coupled to a local video/audio feed received from the user interface 124.

In some embodiments, the conference screen 1920 associated with a user who is currently speaking may be highlighted, for example, by outlining the conference screen 1920 in a colour.

Figure 20:
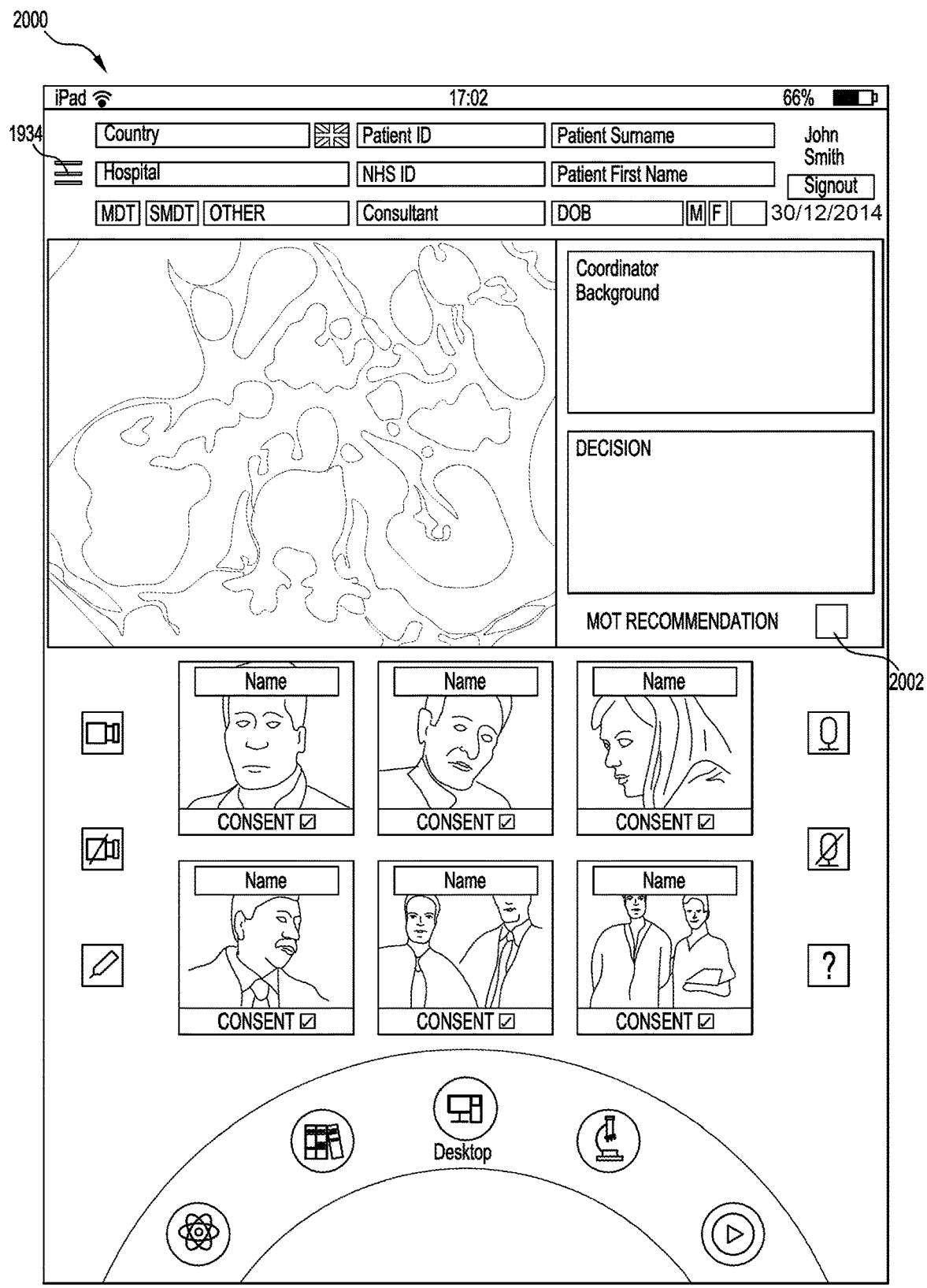

Referring to FIGS. 19 and 20 in particular, the conference window 1918 is associated with a plurality of user selectable options to control the user's participation in the online meeting, including a video on/off option 1922, an audio on/off option 1924, a reverse camera view option 1926, and an mark-up tool 1928.

The video on/off option 1922 is provided to allow the user to control a video feed from a camera of their associated computing device 104, for example, to control whether or not they are visible to other users of the online collaboration environment, i.e. to blank their video feed. The audio on/off option 1924 is provided to allow the user to control the audio signals from a speaker of their associated computing device 104, for example, to control whether or not they are audible to other users of the online collaboration environment, i.e., to mute their audio. The video on/off option 1922 and audio on/off option 1924 provide the user with optional privacy should it be required.

In some embodiments, selection of the video on/off option 1922 and/or audio on/off option 1924 triggers code of the browser application 302 being executed by the processor 120 to transmit a request to the session management module 218 of the collaboration application 204, at 1722, as shown in FIG. 17. For example, the request may include the stream identifier associated with the video/audio feed to be controlled. As depicted in FIG. 18, in response to receiving the request from the browser application 302, the session management module 218 may issue a command, which may include the stream identifier and the meeting session identifier, to the VSC 110 to cause the VSC 110 to turn on/off the audio/video of the stream identifier associated with the computing device 104, at 1816. In some embodiments, a user may have permission to control the audio/video of the stream only being received from the user's user interface and transmitted to the VSC 110, i.e., the stream associated with their own interactions in the online collaboration environment. In some embodiments, a user, such as the coordinator, may have permission to control at least some of the audio/video streams of other computing device(s). In some embodiments, the online collaboration environment provides a user selectable option (not shown) to allow a user, such as a collaborator to send a warning to a speaker to indicate that they have a limited amount of time remaining before their audio/video will be muted/blanked. For example, the conference screen 1920 associated with a user who is currently speaking may be caused to flash for a period of time. The browser application 302 of only the speaker or some or all of the computing devices 104 may receive code from the web server 220 for execution by processor 120 to cause the collaboration display to depict the flashing conference screen 1920.

In some embodiments, a stopwatch (not shown) is incorporated or integrated with the video on/off option 1922 and/or audio on/off option 1924 which is configured to start once the video off option 1922 and/or audio off option 1924 is selected by the user. In some embodiments, as discussed in connection with FIG. 14, in response to receiving an audio/video control request from the browser application 302, the data handling module 210 of the web portal application 202 causes the web server 220 of the collaboration application 204 (directly or via data handling module 216) to transmit code to the browser application 302 of the computing devices 104 associated with the speaker only or to the browser application 302 of some or all of the computing devices 104 for execution by processor 120 to cause the collaboration display to depict the stopwatch (not shown) configured to start once the video on/off option 1404 and/or audio on/off option 1406 is selected by a user using the web portal.

The reverse camera view option 1926 is provided to allow the user to control a camera view of their associated computing device 104 to switch from a forward facing view to a rear facing view.

The mark-up tool 1928, which provides the functionality of an electronic whiteboard marker, is provided to enable the user to mark-up or draw on the collaboration environment display 1900, for example, to highlight aspects of the content displayed in the content display panel 1916. In some embodiments, any marks or lines drawn on the content display panel 1916 may be modified or removed by an authorised user, such as the coordinator. In such embodiments, the authorised user is provided with a user selectable option (not shown) to edit and/or delete users marks or lines. In some embodiments, selection and use of the mark-up tool 1928 triggers code of the browser application 302 being executed by the processor 120 to send an edit/delete request to the data handling module 216, at 1724, as shown in FIG. 17. In response to receiving the edit delete request, the data handling module 216 may process the request and the web server 220 may generate and transmit updated code to the browser applications 302 of the computing devices 204 participating in the online meeting, at 1818. The browser application 302 may receive and generate the updated code to display an updated online environment display 1900, 2000, 2100, 2200, 2300, at 1726, as shown in FIG. 17.

As depicted, the conference screens 1920 each identify the name of the user and display a consent identifier 1930, such as a tick box, to indicate whether or not the user has consented or agreed with the proposed decision. Accordingly, the collaboration environment display 1900 provides a user selectable consent option 1932, such as a recommendation tick box, is provided to allow a user to indicate their approval or consent of the proposed decision, such as a proposed course of action for treatment of the patient, via the user interface 124 of the computing device 104.

In some embodiments, selection of the consent option 1932 by a user triggers code of the browser application 302 being executed by the processor 120 to transmit a consent notification to the data handling module 216 of the collaboration environment application 204, at 1728, as shown in FIG. 17. Referring to FIG. 18, in response to receiving the consent notification, the data handling module 216 may record an indication of the user's approval of the proposed decision in the data record and the web server 220 may transmit code to the browser applications 302 of the computing devices 104 participating in the online collaboration environment for updating the collaboration environment display 1900, 2000, 2100, 2200, 2300 at 1820. Referring again to FIG. 17, the browser application 302 receives code from the web server 220 and updates the collaboration environment display 1900, 2000, 2100, 2200, 2300 on the user interface 126, at 1726.

As shown in collaboration environment display 2000 of FIG. 20, a user selectable store record option 2002 may be provided to allow an authorised user, such as a coordinator, to cause a secure record of the meeting based on the proposed decision presented in the decision panel 1910 to be created and stored in data memory 116 and/or database 108, for example. In some embodiments, the user selectable store record option 2002 may only be activated once all, a majority or a pre-determined quota of the participants have indicated their consent or approval of the proposed decision presented in the decision panel 1910 by selecting the user selectable consent option 1932.

In some embodiments, selection of the store record option 2002 by a user triggers code of the browser application 302 being executed by the processor 120 to transmit a request to create a secure record to the data handling module 216 of the collaboration environment application 204, at 1730, as shown in FIG. 17. In some embodiments, the request to create a secure record may include a file record of a recording of the online collaboration environment including audio and/or video feeds for the case item and/or meeting which may have been captured by the data handling module 216 of the collaboration application 204 of at least one of the computing device(s) 204, such as the computing device 204 associated with the coordinator. In some embodiments, the file record of the recording of the online collaboration environment may not include any interaction by the user with the drop down option 1934 or user selectable case preview option 2202 or details of other cases viewed by the user in the online collaboration environment during the meeting.

Referring to FIG. 18, in response to receiving the request to create a secure record, the data handling module 216 may add the file record of the recording of the online collaboration environment to the data record and may lock the file record to prevent any further additions, deletions or modifications to the data record, at 1822.

The data handling module 216 may also cause the web server 220 to transmit code to the browser application 302 to update the collaboration environment display to show display 2100 at 1820. Referring again to FIG. 17, the browser application 302 receives code from the web server 220 and generates collaboration environment display 2100 on the user interface 126, at 1726.

The collaboration environment display 2100 of FIG. 21 shows an MDT record 2102 in content display panel 1916. The MDT record 2102 is associated with and provides details of the secured record of the meeting stored in data memory 116 and/or database 108.

Figure 22:
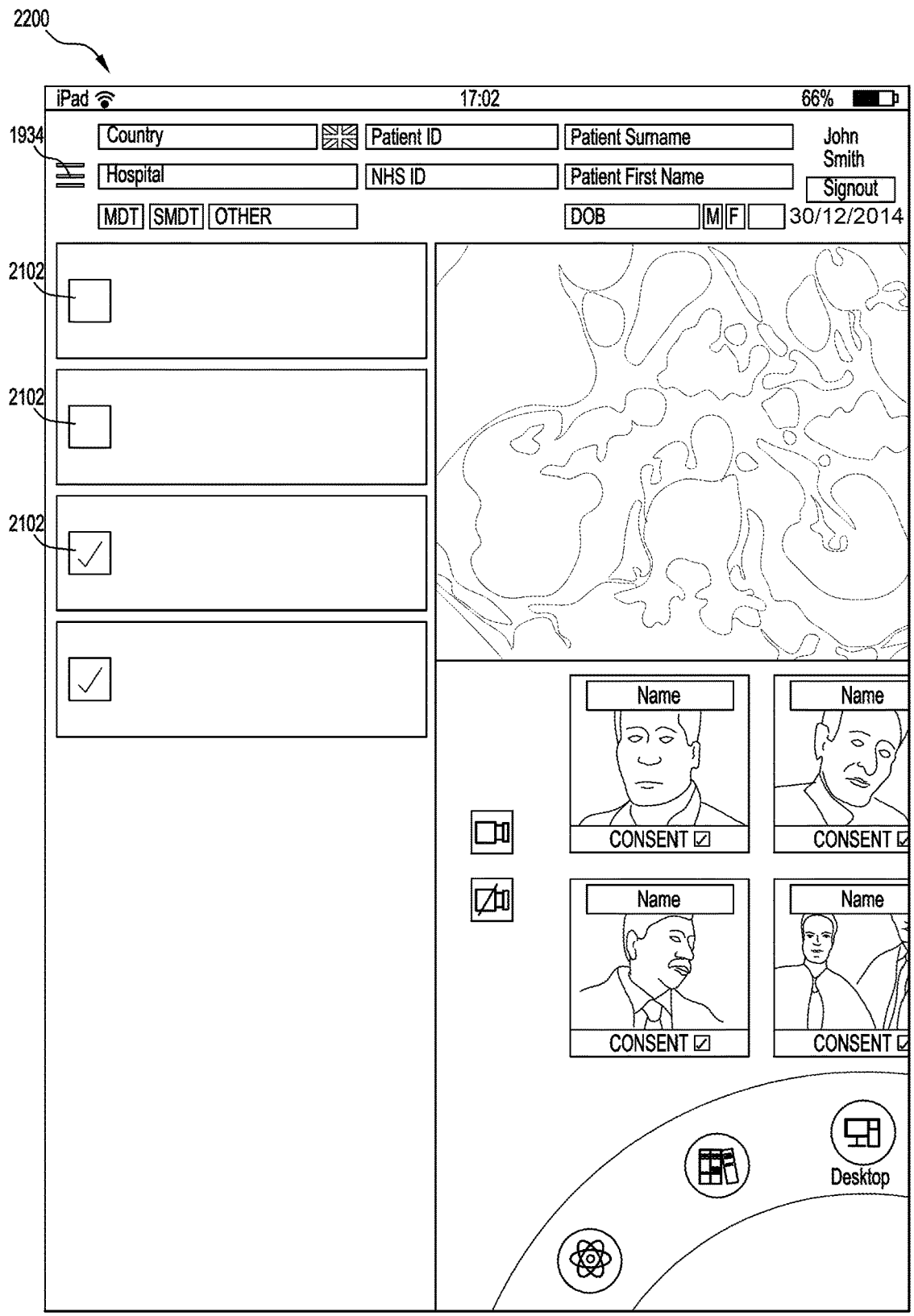

As shown in FIGS. 19 to 23, the collaboration environment displays 1900 2000, 2100, 2200, 2300 show a drop down option 1934, which when selected by a user, causes the bowler application to generate collaboration environment display 2200 as shown in FIG. 22. For example, selection of the drop down option 1934 may trigger code of the browser application 302 being executed by the processor 120 to request and receive content from the web server 220, at 1718, 1720 of FIG. 17 and 1818 of FIG. 18, or may execute an applet within the code of the browser application 302 to display information associated with the selected drop down option 1934.

Figure 23:
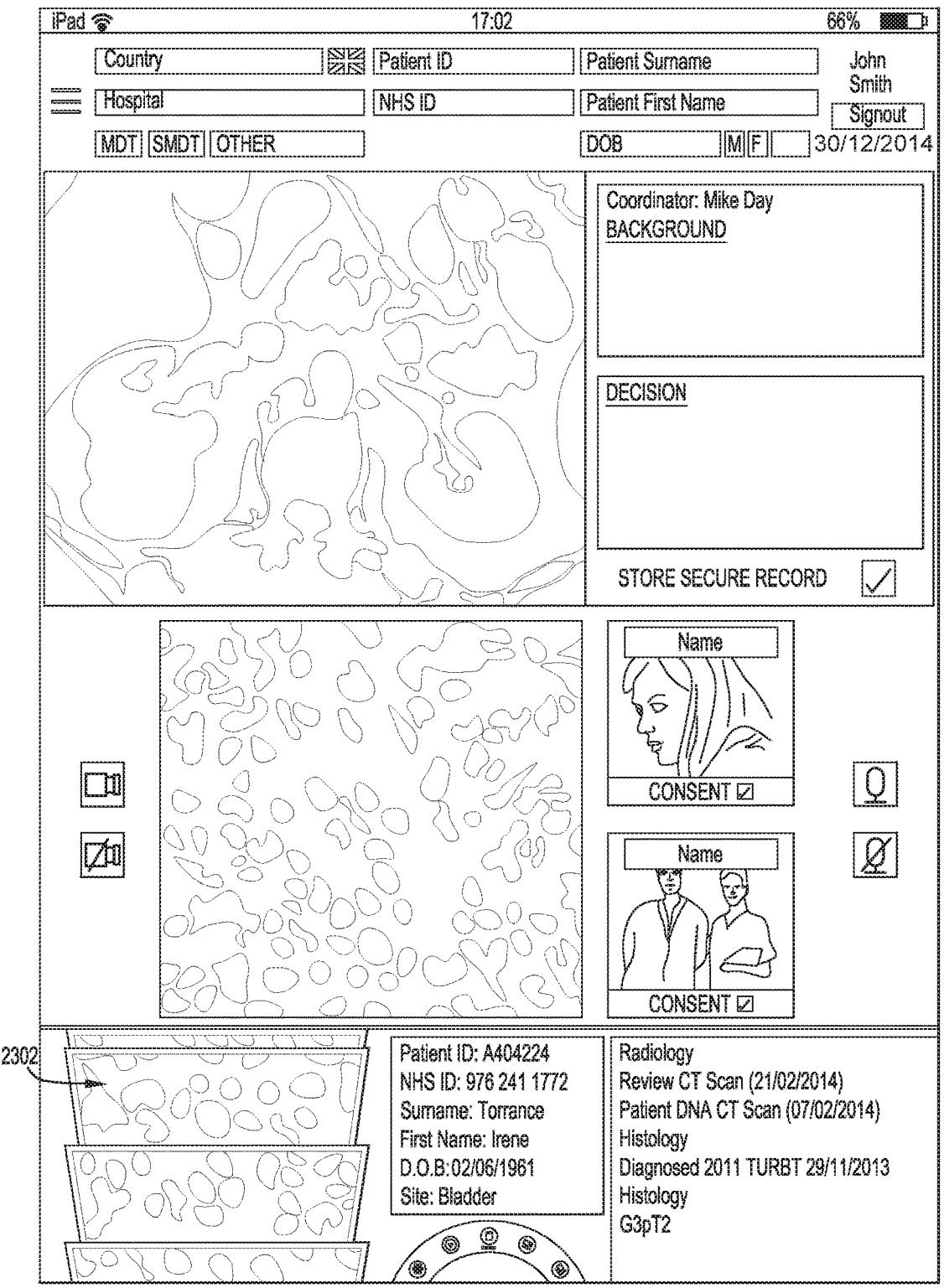

The collaboration environment display 2200 displays a user selectable case preview option 2202 of other cases that have been scheduled for the online meeting and may include cases which have been discussed and for which a secure record has been generated and cases which are yet to be discussed. As depicted the case preview option 2202 may include a synopsis of the case and an indication of whether or not a decision was made for that case. Selection of a case preview option 2202 triggers code of the browser application 302 being executed by the processor 120 to send a content request, which may include a case identifier, to the data handling module 216 of the collaboration application 204, at 1718, as shown in FIG. 17. In response to the content request, the data handling module 216 may retrieve case information from the data record associated with the selected case preview option 2202 and transmit the content to the browser application 302, at 1814, as shown in FIG. 18. For example, the data handling module 216 may transmit the content to the browser application 302 that requested the content and not to the browser applications of the other computing devices 104 participating in the online collaboration environment. Referring again to FIG. 17, the browser application 302 may receive the content from the data handling module 216 and display the content in the online collaboration environment display, for example, as an overlay 2302, as shown in the collaboration environment display 2300, as depicted in FIG. 23. In some embodiments, a user may be allowed to interact with the content to rearranged a display of the content on the user interface 126.

The collaboration environment display 2200 may also provide a user selectable conclusion option (not shown) to end the meeting. For example, in some embodiments, selection of the conclusion option (not shown) triggers code of the browser application 302 being executed by the processor 120 to send a notification to the data handling module 216, at 1732 of FIG. 17 which may be received by the data handling module 216 and cause the conclusion or termination of the online collaboration environment, at 1824. In some embodiments, only authorised users, such as the coordinator, have the necessary permissions to cause a termination of an online meeting.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An online collaboration system comprising:
at least one server in communication with multiple client computing devices over a communication network, the at least one server executing program code to host an online collaborative environment in which users of the client computing devices can collaborate;
wherein the at least one server is configured to execute program code to:
facilitate an online meeting between the users of the client computing devices in the online collaboration environment;
display a plurality of conference panels on a user interface of at least some of the multiple client computing devices, each conference panel configured to depict a real-time video stream associated with one of the client computing devices participating in the online meeting and a consent identifier to indicate whether the user of the client computing device has consented to a proposed course of action;
display at least one display panel on the user interface of the at least some of the multiple client computing devices, wherein the at least one display panel of each user interface is configured to display common shared information relating to the online meeting;
display a proposed course of action in a window of the online collaborative environment;
provide at least one user selectable consent option to allow a user to submit a non-textual indication of agreement with the displayed proposed course of action by selecting the user selectable consent option via the user interface;
in response to a user submitting an indication of agreement with the displayed proposed course of action by selecting the user selectable consent option via the user interface, automatically cause a consent notification to be sent to a data handling module, and update the consent identifier associated with the user's client computing device;
provide at least one user selectable option to allow a secure record to be created, wherein the secure record comprises a recording of at least a portion of an online meeting relating to the proposed course of action conducted in the online collaboration environment, and wherein the at least one user selectable option to allow a secure record to be created is activated once a pre-determined quota of users have indicated agreement with the displayed proposed course of action by selecting the at least one user selectable consent option via the user interface; and
in response to a user selecting the user selectable option to allow a secure record to be created, add a file record of the recording of at least a portion of an online meeting relating to the proposed course of action conducted in the online collaboration environment to a data record, and lock the data record to prevent any further additions, deletions or modifications to the data record.

2. The online collaboration system of claim 1, wherein the at least one server executes program code to provide at least one user selectable display option to allow display of information in the display panel.

3. The online collaboration system of claim 2, wherein the at least one user selectable display option to allow display of information in the display panel further allows selection of the information from a data record.

4. The online collaboration system of claim 1, wherein the at least one server executes program code to provide at least one user selectable control option to allow control of the user's participation in the online collaborative environment.

5. The online collaboration system of claim 4, wherein the at least one user selectable control option comprises at least one of a video stream control option, an audio stream control option, a camera view control option and a mark-up tool control option.

6. The online collaboration system of claim 4, wherein the at least one user selectable control option comprises a media control option and in response to selection of the media control option, the at least one server executes program code to control a broadcast of a media stream associated with the user to other client computing devices participating in the online collaborative environment.

7. The online collaboration system of claim 6, wherein the at least one server executes program code to transmit a media control request to a video communications server to control the broadcast of the media stream, wherein the video communications server is configured to receive and relay media streams to and from the multiple client computing devices associated with an online meeting being held in the online collaborative environment.

8. The online collaboration system of claim 4, wherein the at least one user selectable control option comprises a mark-up tool control option and in response to selection of the mark-up tool control option, the at least one server executes program code to display interactions of the user with the online collaborative environment in the online collaborative environment.

9. The online collaboration system of claim 1, wherein in response to receiving the consent notification, the data handling module is configured to automatically record an indication of agreement received via the at least one user selectable consent option in the data record to form part of the secure record.

10. The online collaboration system of claim 1, wherein selecting the user selectable consent option comprises checking the user selectable consent option.

11. The online collaboration system of claim 10, wherein the user selectable consent option comprises a tick box.

12. A web portal system comprising:
at least one server in communication with multiple client computing devices over a communication network, the at least one server executing program code to provide a web portal for controlling user participation in an online collaborative environment being hosted by the at least one server, wherein the online collaborative environment allows users of the client computing devices to collaborate as participants;
wherein the at least one server executes program code to:
display a plurality of conference panels on a user interface of at least some of the client computing devices, each conference panel configured to depict a real-time video stream associated with one of the client computing devices participating in the online collaborative environment and a consent identifier to indicate whether the user of the client computing device has consented to a proposed course of action;
provide at least one user selectable control option to allow a user to control at least one other user's participation in the online collaborative environment by controlling a broadcast of a media stream associated with the other user to the client computing devices, display a proposed course of action in a window of the online collaborative environment;
provide at least one user selectable consent option to allow a user to submit a non-textual indication of agreement with the displayed proposed course of action by selecting the user selectable consent option via a user interface;
in response to a user submitting an indication of agreement with the displayed proposed course of action by selecting the user selectable consent option via the user interface, automatically cause a consent notification to be sent to a data handling module, and update the consent identifier associated with the user's client computing device;
provide at least one user selectable option to allow a secure record to be created, wherein the secure record comprises a recording of at least a portion of an online meeting relating to the proposed course of action conducted in the online collaboration environment, and wherein the at least one user selectable option to allow a secure record to be created is activated once a pre-determined quota of users have indicated agreement with the displayed proposed course of action by selecting the at least one user selectable consent option via the user interface; and
in response to a user selecting the user selectable option to allow a secure record to be created, add a file record of the recording of at least a portion of an online meeting relating to the proposed course of action conducted in the online collaboration environment to a data record, and locking the data record to prevent any further additions, deletions or modifications to the data record.

13. The web portal system of claim 12, wherein in response to selection of the at least one user selectable control, the at least one server executes program code to cause a media stream control request to be transmitted to a video communications server to control the broadcast of the media stream, wherein the video communications server is configured to receive and relay media streams to and from the multiple client computing devices associated with an online meeting being held in the online collaborative environment.

14. The web portal system of claim 13, wherein the media stream control request comprises a stream identifier associated with the participant's computing device.

15. The web portal system of claim 12, wherein the at least one server executes program code to provide at least one user selectable schedule option to allow a user to schedule an online meeting for the online collaborative environment.

16. The web portal system of claim 15, wherein in response to selection of the at least one user selectable schedule option, the at least one server executes program code to cooperate with a video communications server to enable the video communications server to receive and relay media streams to and from the multiple client computing devices associated with the online meeting.

17. The web portal system of claim 16, wherein the at least one server executes program code to cooperate with a video communications server to determine a meeting session identifier for the schedule online meeting.

18. The web portal system of claim 17, wherein the at least one server executes program code to provide the client computing devices associated with the online meeting with the meeting session identifier to enable the client computing devices to subscribe to the video communications server to receive media streams associated with the meeting session identifier.

19. The web portal system of claim 12, wherein the data record is remotely located from the client computing device associated with the user.

20. The web portal system of any one of claim 12, wherein the at least one server executes program code to provide at least one user selectable invite option to invite users of the client computing devices to collaborate as participants in the online meeting, and in response to selection of the at least one user selectable invite option, the at least one server executes program code to transmit at least one invitation to a user of one of the multiple client computing devices.

21. An online collaboration system comprising:
at least one server in communication with multiple client computing devices over a communication network, the at least one server executing program code to host an online collaborative environment in which users of the client computing devices can collaborate,
wherein the at least one server executes program code to facilitate a real-time multimedia meeting between the users of the client computing devices in the online collaboration environment to allow discussion of a proposed course of action and determination of an agreed outcome by:
displaying a plurality of conference panels on a user interface of at least some of the client computing devices, each conference panel configured to depict a real-time video stream associated with one of the client computing devices participating in the real-time meeting and a consent identifier to indicate whether the user of the client computing device has consented to a proposed course of action,
displaying a proposed course of action in a window of the online collaborative environment,
providing at least one user selectable consent option to allow a user to submit a non-textual indication of agreement with the displayed proposed course of action by selecting the user selectable consent option via a user interface,
in response to a user submitting an indication of agreement with the displayed proposed course of action by selecting the user selectable consent option via the user interface, automatically causing a consent notification to be sent to a data handling module, and update the consent identifier associated with the user's client computing device,
providing at least one user selectable option to allow a secure record to be created; and
in response to a user selecting the user selectable option to allow a secure record to be created, adding a file record of the recording of at least a portion of an online meeting relating to the proposed course of action conducted in the online collaboration environment to a data record, and locking the data record to prevent any further additions, deletions or modifications to the data record,
wherein the secure record comprises a recording of at least a portion of an online meeting relating to the proposed course of action conducted in the online collaboration environment, and
wherein the at least one user selectable option to allow a secure record to be created is activated once a predetermined quota of users have indicated agreement with the displayed proposed course of action by selecting the at least one user selectable consent option via the user interface.

* * * * *